US012765843B2

(12) United States Patent
Capodilupo et al.

(10) Patent No.: US 12,765,843 B2
(45) **Date of Patent: *Oct. 20, 2026**

(54) DETERMINING SLEEP NEED FROM PHYSIOLOGICAL MEASUREMENTS

(71) Applicant: Whoop, Inc., Boston, MA (US)

(72) Inventors: John Vincenzo Capodilupo, Boston, MA (US); Behnoosh Tavakoli, Needham, MA (US); Mostafa Ghannad-Rezaie, Malden, MA (US)

(73) Assignee: Whoop, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/225,049

(22) Filed: Jun. 2, 2025

(65) Prior Publication Data

US 2025/0288255 A1 Sep. 18, 2025

Related U.S. Application Data

(63) Continuation of application No. 18/634,281, filed on Apr. 12, 2024, now Pat. No. 12,318,226, which is a
(Continued)

(51) Int. Cl.
*A61B 5/00* (2006.01)
*A61B 5/0205* (2006.01)
(Continued)

(52) U.S. Cl.
CPC ........ *A61B 5/7267* (2013.01); *A61B 5/02055* (2013.01); *A61B 5/02416* (2013.01);
(Continued)

(58) Field of Classification Search
CPC .............. A61B 5/7267; A61B 5/02055; A61B 5/02416; A61B 5/02438; A61B 5/681;
(Continued)

(56) References Cited

U.S. PATENT DOCUMENTS 4,307,727 A 12/1981 Haynes
9,743,848 B2 8/2017 Breslow et al.
(Continued)

FOREIGN PATENT DOCUMENTS

WO WO-2010042615 4/2010

OTHER PUBLICATIONS

Ge, Z. et al., "Evaluating the Accuracy of Wearable Heart Rate Monitors", 2016 IEEE NPL-88 Sep. 30, 2016 , 6 pages.
(Continued)

*Primary Examiner* — Joel Lamprecht
(74) *Attorney, Agent, or Firm* — Strategic Patents, P.C.

(57) ABSTRACT

Sleep need for a user is assessed using continuous physiological data from a wearable monitor. In particular, by calculating a first sleep debt metric based on user strain and a second sleep debt metric based on accumulated sleep debt, an objective metric can be obtained that estimates an amount of sleep needed by the user in a next sleep period. This approach takes advantage of multiple modes of information embedded in the physiological data, such as a sleep and exercise patterns for a user over one or more preceding days.

20 Claims, 11 Drawing Sheets

Related U.S. Application Data continuation of application No. 17/536,331, filed on Nov. 29, 2021, now Pat. No. 11,986,323, which is a continuation of application No. 16/163,441, filed on Oct. 17, 2018, now Pat. No. 11,185,292.

(60) Provisional application No. 62/573,683, filed on Oct. 17, 2017.

(51) Int. Cl.

| | |
|---|---|
| ***A61B 5/024*** | (2006.01) |
| ***G06F 18/243*** | (2023.01) |
| *A61B 5/0245* | (2006.01) |
| *A61B 5/0533* | (2021.01) |
| *A61B 5/08* | (2006.01) |
| *A61B 5/11* | (2006.01) |
| *A61B 5/145* | (2006.01) |

(52) U.S. Cl.

CPC .......... *A61B 5/02438* (2013.01); *A61B 5/681* (2013.01); *A61B 5/7221* (2013.01); *G06F 18/24323* (2023.01); *A61B 5/0022* (2013.01); *A61B 5/02405* (2013.01); *A61B 5/0245* (2013.01); *A61B 5/0533* (2013.01); *A61B 5/0816* (2013.01); *A61B 5/1118* (2013.01); *A61B 5/14542* (2013.01); *A61B 5/4812* (2013.01); *A61B 5/4815* (2013.01); *A61B 5/4866* (2013.01); *A61B 5/6831* (2013.01); *A61B 2560/0209* (2013.01); *A61B 2560/0223* (2013.01); *A61B 2560/0242* (2013.01); *A61B 2562/0219* (2013.01)

(58) Field of Classification Search

CPC . A61B 5/7221; A61B 5/0022; A61B 5/02405; A61B 5/0245; A61B 5/0533; A61B 5/0816; A61B 5/1118; A61B 5/14542; A61B 5/4812; A61B 5/4815; A61B 5/4866; A61B 5/6831; A61B 2560/0209; A61B 2560/0223; A61B 2560/0242; A61B 2562/0219; G06F 18/24323; G16H 50/70

See application file for complete search history.

(56) References Cited

U.S. PATENT DOCUMENTS

| | | | | |
|---|---|---|---|---|
| 9,750,415 | B2 | 9/2017 | Breslow et al. | |
| 9,750,429 | B1 | 9/2017 | Sackner et al. | |
| 11,185,292 | B2 * | 11/2021 | Capodilupo | A61B 5/7267 |
| 11,197,633 | B2 | 12/2021 | Heneghan et al. | |
| 11,986,323 | B2 * | 5/2024 | Capodilupo | A61B 5/7267 |
| 12,318,226 | B2 * | 6/2025 | Capodilupo | A61B 5/7267 |
| 2013/0190635 | A1 | 7/2013 | Shen et al. | |
| 2014/0275852 | A1 | 9/2014 | Hong et al. | |
| 2014/0350356 | A1 | 11/2014 | Ahmed et al. | |
| 2016/0374567 | A1 | 12/2016 | Capodilupo et al. | |
| 2019/0110755 | A1 | 4/2019 | Capodilupo et al. | |
| 2022/0079530 | A1 | 3/2022 | Capodilupo et al. | |
| 2024/0252121 | A1 | 8/2024 | Capodilupo et al. | |

OTHER PUBLICATIONS

Hwang, Sungjoo et al., "Feasibility analysis of heart rate monitoring of construction workers using a photoplethysmography (PPG) sensor embedded in a wristband-type activity tracker", NPL-89 Aug. 27, 2016 , 10 pages.

Jindal, Vasu , "Integrating Mobile and Cloud for PPG Signal Selection to Monitor Heart Rate During Intensive Physical Exercise", 2016 IEEE/ACM International Conference on Mobile Software Engineering and Systems NPL-90 May 16, 2016 , 2 pages.

Zhang, Zhilin et al., "Troika: A General Framework for Heart Rate Monitoring Using Wrist-Type Photoplethysmographic Signals During Intensive Physical Exercise", NPL-110 Feb. 2015 , 10 pages.

USPTO, , "U.S. Appl. No. 16/163,441 Non-Final Office Action mailed Mar. 2, 2021", NPL-116 , 9 pages.

USPTO, , "U.S. Appl. No. 16/163,441 Notice of Allowance mailed Sep. 23, 2021", NPL-117 , 8 pages.

USPTO, , "U.S. Appl. No. 17/536,331 Non-Final Office Action mailed Aug. 31, 2023", NPL-270 , 11 pages.

USPTO, , "U.S. Appl. No. 17/536,331 Notice of Allowance mailed Feb. 1, 2024", NPL-271 , 7 pages.

USPTO, , "U.S. Appl. No. 18/634,281 Notice of Allowance mailed Apr. 28, 2025", , 9 pages.

EPO, , "EP Application No. 18868234.8 Examination Report mailed Mar. 27, 2023", NPL-176 , 8 pages.

EPO, , "EP Application No. 18868234.8 Summons to Attend Oral Proceedings mailed Feb. 18, 2025", , 9 pages.

EPO, , "EP Application No. 18868234.8 Supplemental Search Report mailed Jun. 4, 2021", NPL-91 , 9 pages.

ISA, , "PCT Application No. PCT/US18/56358 International Preliminary Report on Patentability mailed Apr. 30, 2020", NPL-71 , 10 Pages.

ISA, , "PCT Application No. PCT/US18/56358 International Search Report and Written Opinion mailed Dec. 27, 2018", NPL-59 , 11 pages.

* cited by examiner

DETERMINING SLEEP NEED FROM PHYSIOLOGICAL MEASUREMENTS

CROSS-REFERENCE TO RELATED APPLICATIONS

This application is a continuation of U.S. patent application Ser. No. 18/634,281 filed on Apr. 12, 2024, which is a continuation of U.S. patent application Ser. No. 17/536,331 filed on Nov. 29, 2021 (now U.S. Pat. No. 11,986,323), which is a continuation of U.S. patent application Ser. No. 16/163,441 filed on Oct. 17, 2018 (now U.S. Pat. No. 11,185,292), which claims the benefit of U.S. Provisional Patent Application No. 62/573,683 filed on Oct. 17, 2017, where the contents of each of the foregoing applications are hereby incorporated by reference in their entirety.

This application is also related to the following commonly-owned patent applications, each of which is hereby incorporated by reference in its entirety: U.S. patent application Ser. No. 14/290,065 filed on May 29, 2014, and U.S. patent application Ser. No. 15/265,761 filed on Sep. 14, 2016 (now U.S. Pat. No. 9,596,997).

BACKGROUND

Wearable devices can be used for physiological monitoring. While convenient, these devices are susceptible to a variety of different types of errors. For example, data quality may vary according to where a device is positioned on the body, whether the device is securely strapped to the body, the type of activity a user is engaged in, and so forth. There remains a need for real-time, data-driven assessments of data quality to accompany physiological data acquisition from wearable monitoring devices.

SUMMARY

A model of data quality is derived for physiological monitoring with a wearable device by comparing data from the wearable device to concurrent data acquisition from a ground truth device such as a chest strap or electrocardiography (EKG) heart rate monitor. With this comparative data, a machine learning model or the like may be derived to prospectively evaluate data quality based on the data acquisition context, as determined, for example, by other sensor data and signals from the wearable device.

In one aspect, a method disclosed herein includes obtaining calibrated heart rate data from a number of subjects using one or more chest strap type sensors; obtaining uncalibrated heart rate data from the number of subjects concurrently with the calibrated heart rate data using one or more physiological monitors of a wrist-worn photoplethysmography type; obtaining feature data from one or more sensors of the one or more physiological monitors of the wrist-worn photoplethysmography type concurrently with the calibrated heart rate data and the uncalibrated heart rate data, the feature data characterizing a plurality of features of a data acquisition context for a corresponding one of the physiological monitors of the wrist-worn photoplethysmography type; associating a quality metric for the uncalibrated heart rate data with the feature data based on whether, for each data acquisition context, the uncalibrated heart rate data is within a predetermined threshold of the calibrated heart rate data; creating a quality estimator engine to evaluate a likelihood of the uncalibrated heart rate data being accurate based on the feature data; receiving second uncalibrated heart rate data and second feature data from a second physiological monitor of the wrist-worn photoplethysmography type; determining a probability that the second uncalibrated heart rate data is accurate for a window of measurements by calculating a conditional probability that the second uncalibrated heart rate data is accurate based on the second feature data over a distribution of values for the calibrated heart rate data within the window of measurements based on the quality estimator engine; and associating the probability with the window as a measure of quality for the uncalibrated heart rate data within the window.

The feature data may include at least one signal used to estimate a heart rate using the uncalibrated heart rate data. The feature data may include at least one value derived from a signal from one of the physiological monitors of the wrist-worn photoplethysmography type. The feature data may include a signal derived from a motion sensor of one of the physiological monitors of the wrist-worn photoplethysmography type. The quality metric may be a one when the uncalibrated heart rate data is within the predetermined threshold of the uncalibrated heart rate data and a zero when the uncalibrated heart rate data is not within the predetermined threshold of the uncalibrated heart rate data. Creating the quality estimator engine may include training a machine learning random forest to estimate the quality metric for a set of feature data. The predetermined threshold may include a number of beats per minute for a heart rate. The method may further include providing feedback to a user concerning an adjustment to the second physiological monitor based on the measure of quality. The adjustment may include a change in a position of the second physiological monitor. The adjustment may include a change in a tension of a band for the second physiological monitor. The method may further include characterizing a user of the second physiological monitor, identifying a subset of the number of subjects similar to the user, and associating the quality metric for the uncalibrated heart rate data with the feature data for the subset of the number of subjects similar to the user.

In another aspect, a method disclosed herein includes obtaining data for a number of subjects, the data including calibrated physiological data from a first type of physiological monitors assumed to be accurate, uncalibrated physiological data from a second type of physiological monitors of unknown accuracy, and feature data characterizing a timewise data acquisition context for the uncalibrated physiological data; training a quality estimator engine to determine a quality of the uncalibrated physiological data based on the feature data and a difference between the uncalibrated physiological data and the calibrated physiological data; receiving physiological data and feature data from a different one of the second type of physiological monitors; calculating a probability that the physiological data is accurate for a window of measurements by applying the quality estimator engine to a distribution of values for the physiological data and corresponding values for the feature data; and associating the probability with the window as a measure of quality for the physiological data within the window.

The uncalibrated physiological data may include heart rate data. The second type of physiological monitors may include a photoplethysmography device. The method may further include conditionally processing the physiological data based on the measure of quality. The method may further include providing user feedback based on the measure of quality. The quality estimator engine may include a machine learning engine.

In another aspect, a computer program product disclosed herein includes computer executable code embodied in a non-transitory computer readable medium that, when executing on a wearable device, performs the steps of: receiving physiological data and feature data from one or more sensors of the wearable device, the physiological data characterizing a physiological measurement for a user of the wearable device and the feature data characterizing a timewise data acquisition context for the physiological data; storing a quality estimator engine that calculates a probability that a measurement of the physiological data is accurate based on corresponding feature data; calculating a second probability that the physiological data is accurate for a window of measurements by applying the quality estimator engine to a distribution of values for the physiological data and corresponding values for the feature data; and associating the second probability with the window as a measure of quality for the physiological data within the window.

The quality estimator engine may include a decision tree trained to estimate the quality metric for a set of feature data using a training set for which the quality metric is a one when a measurement of the physiological data is within a predetermined threshold of a second measurement of known accuracy captured concurrently with the measurement, and the quality metric is a zero when the measurement is not within the predetermined threshold of the second measurement.

In another aspect, a wearable device disclosed herein includes a wrist strap; one or more sensors for capturing physiological data characterizing a physiological measurement for a user of the wearable device and feature data characterizing a timewise data acquisition context for the physiological data; a memory storing a quality estimator engine configured to calculate a probability that a measurement of the physiological data is accurate based on corresponding feature data; a processor configured by computer executable code to perform the steps of receiving physiological data and feature data from the one or more sensors, calculating a second probability that the physiological data is accurate for a window of measurements by applying the quality estimator engine to a distribution of values for the physiological data and corresponding values for the feature data, and storing the second probability as a measure of quality for the physiological data within the window.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures. The figures are not necessarily to scale, emphasis instead being placed upon illustrating the principles of the devices, systems, and methods described herein.

DETAILED DESCRIPTION

Figure 1:
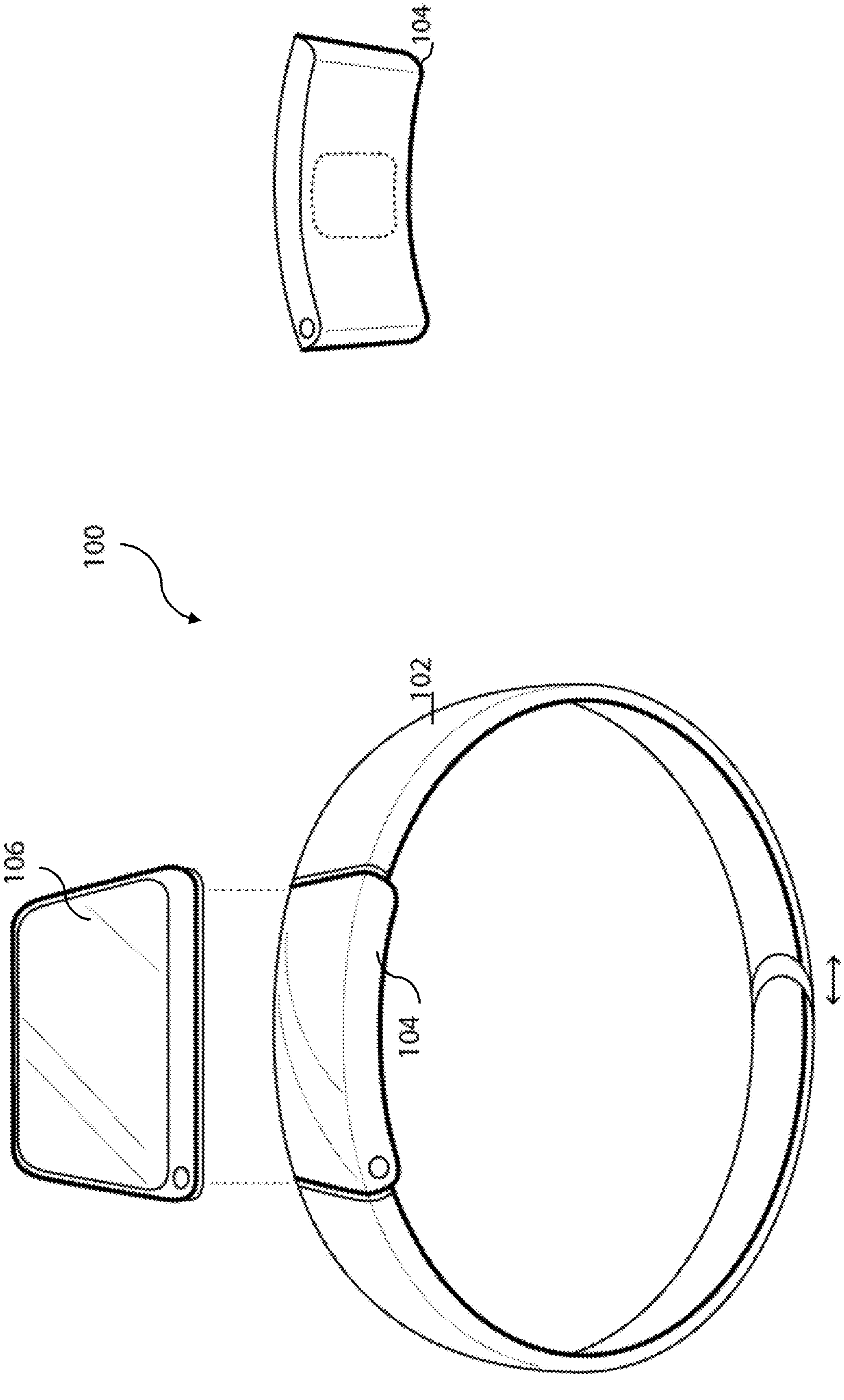
FIG. 1 illustrates front and back perspective views of a wearable system configured as a bracelet including one or more straps.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitations of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as including any deviation as would be appreciated by one of ordinary skill in the art to operate satisfactorily for an intended purpose, or where applicable, any acceptable range of deviation appropriate to a measurement of the numerical value or achievable by instrumentation used to measure the amount. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "above," "below," and the like, are words of convenience and are not to be construed as limiting terms.

Exemplary embodiments provide physiological measurement systems, devices and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on an appendage or extremity of a user, for example, wrist, ankle, and the like. Exemplary systems are wearable and enable real-time and continuous monitoring of heart rate without the need for a chest strap or other bulky equipment which could otherwise cause discomfort and prevent continuous wearing and use. The system may determine the user's heart rate without the use of electrocardiography and without the need for a chest strap. Exemplary systems can thereby be used in not only assessing general well-being but also in continuous monitoring of fitness. Exemplary systems also enable monitoring of one or more physiological parameters in addition to heart rate including, but not limited to, body temperature, heart rate variability, motion, sleep, stress, fitness level, recovery level, effect of a workout routine on health and fitness, caloric expenditure, and the like.

A health or fitness monitor that includes bulky components may hinder continuous wear. Existing fitness monitors often include the functionality of a watch, thereby making the health or fitness monitor quite bulky and inconvenient for continuous wear. Accordingly, one aspect is directed to providing a wearable health or fitness system that does not include bulky components, thereby making the bracelet slimmer, unobtrusive and appropriate for continuous wear. The ability to continuously wear the bracelet further allows continuous collection of physiological data, as well as continuous and more reliable health or fitness monitoring. For example, embodiments of the bracelet disclosed herein allow users to monitor data at all times, not just during a fitness session. In some embodiments, the wearable system may or may not include a display screen for displaying heart rate and other information. In other embodiments, the wearable system may include one or more light emitting diodes (LEDs) to provide feedback to a user and display heart rate selectively. In some embodiments, the wearable system may include a removable or releasable modular head that may provide additional features and may display additional information. Such a modular head can be releasably installed on the wearable system when additional information display is desired, and removed to improve the comfort and appearance of the wearable system. In other embodiments, the head may be integrally formed in the wearable system.

Exemplary embodiments also include computer-executable instructions that, when executed, enable automatic interpretation of one or more physiological parameters to assess the cardiovascular intensity experienced by a user (embodied in an intensity score or indicator) and the user's recovery after physical exertion or daily stress given sleep and other forms of rest (embodied in a recovery score). These indicators or scores may be stored and displayed in a meaningful format to assist a user in managing his health and exercise regimen.

In an exemplary technique of data transmission, data collected by a wearable system may be transmitted directly to a cloud-based data storage, from which data may be downloaded for display and analysis on a website. In another exemplary technique of data transmission, data collected by a wearable system may be transmitted via a mobile communication device application to a cloud-based data storage, from which data may be downloaded for display and analysis on a website.

The term "user" as used herein, refers to any type of animal, human or non-human, whose physiological information may be monitored using an exemplary wearable physiological monitoring system. The term "body," as used herein, refers to the body of a user.

The term "continuous," as used herein in connection with heart rate data collection, refers to collection of heart rate data at a sufficient frequency to enable detection of every heart beat and also refers to collection of heart rate data continuously throughout the day and night.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

Exemplary embodiments provide wearable physiological measurements systems that are configured to provide continuous measurement of heart rate. Exemplary systems are configured to be continuously wearable on an appendage, for example, wrist or ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photo-resistor, a photo-transistor, a photo-diode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts (or with other optical data of another wavelength).

FIG. 1 illustrates front and back perspective views of one embodiment of a wearable system configured as a bracelet 100 including one or more straps 102. The bracelet is sleek and lightweight, thereby making it appropriate for continuous wear. The bracelet may or may not include a display screen, e.g., a screen 106 such as a light emitting diode (LED) display for displaying any desired data (e.g., instantaneous heart rate).

As shown in FIG. 1, the wearable system may include components configured to provide various functions such as data collection and streaming functions of the bracelet. In some embodiments, the wearable system may include a button underneath the wearable system. In some embodiments, the button may be configured such that, when the wearable system is properly tightened to one's wrist, the button may press down and activate the bracelet to begin storing information. In other embodiments, the button may be disposed and configured such that it may be pressed manually at the discretion of a user to begin storing information or otherwise to mark the start or end of an activity period such as sleep. In some embodiments, the button may be held to initiate a time stamp and held again to end a time stamp, which may be transmitted, directly or through a mobile communication device application, to a website as a time stamp.

The wearable system may include a heart rate monitor. In one example, the heart rate may be detected from the radial artery. Thus, the wearable system may include a pulse sensor. In one embodiment, the wearable system may be configured such that, when a user wears it around their wrist and tightens it, the sensor portion of the wearable system is secured over the user's radial artery or other blood vessel. Secure connection and placement of the pulse sensor over the radial artery or other blood vessel may allow measurement of heart rate and pulse. It will be understood that this configuration is provided by way of example only, and that other sensors, sensor positions, and monitoring techniques may also or instead be employed without departing from the scope of this disclosure.

In some embodiments, the pulse or heart rate may be taken using an optical sensor coupled with one or more light emitting diodes (LEDs), all directly in contact with the user's wrist. The LEDs are provided in a suitable position from which light can be emitted into the user's skin. In one example, the LEDs mounted on a side or top surface of a circuit board in the system to prevent heat buildup on the LEDs and to prevent burns on the skin. The circuit board may be designed with the intent of dissipating heat, e.g., by including thick conductive layers, exposed copper, heatsink, or similar. In one aspect, the pulse repetition frequency is such that the amount of power thermally dissipated by the LED is negligible. Cleverly designed elastic wrist straps can ensure that the sensors are always in contact with the skin and that there is a minimal amount of outside light seeping into the sensors. In addition to the elastic wrist strap, the design of the strap may allow for continuous micro adjustments (no preset sizes) in order to achieve an optimal fit, and a floating sensor module. The sensor module may be free to move with the natural movements caused by flexion and extension of the wrist.

In some embodiments, the wearable system may be configured to record other physiological parameters including, but not limited to, skin temperature (using a thermometer), galvanic skin response (using a galvanic skin response sensor), motion (using one or more multi-axes accelerometers and/or gyroscope), and the like, and environmental or contextual parameters, e.g., ambient temperature, humidity, time of day, and the like. In an implementation, sensors are used to provide at least one of continuous motion detection, environmental temperature sensing, electrodermal activity (EDA) sensing, galvanic skin response (GSR) sensing, and the like. In this manner, an implementation can identify the cause of a detected physiological event. Reflectance PhotoPlethysmoGraphy (RPPG) may be used for the detection of cardiac activity, which may provide for non-intrusive data collection, usability in wet, dusty and otherwise harsh environments, and low power requirements. For example, as explained herein, using the physiological readouts of the device and the analytics described herein, an "Intensity Score" (e.g., 0-21) (e.g., that measures a user's recent exertion), a "Recovery Score" (e.g., 0-100%), and "Sleep Score" (e.g., 0-100) may together measure readiness for physical and psychological exertion.

In some embodiments, the wearable system may further be configured such that a button underneath the system may be pressed against the user's wrist, thus triggering the system to begin one or more of collecting data, calculating metrics and communicating the information to a network. In some embodiments, the sensor used for, e.g., measuring heart rate or GSR or any combination of these, may be used to indicate whether the user is wearing the wearable system or not. In some embodiments, power to the one or more LEDs may be cut off as soon as this situation is detected, and reset once the user has put the wearable system back on their wrist.

The wearable system may include one, two or more sources of battery life, e.g., two or more batteries. In some embodiments, it may have a battery that can slip in and out of the head of the wearable system and can be recharged using an included accessory. Additionally, the wearable system may have a built-in battery that is less powerful. When the more powerful battery is being charged, the user does not need to remove the wearable system and can still record data (during sleep, for example).

In exemplary embodiments, the wearable system is enabled to automatically detect when the user is asleep, awake but at rest and exercising based on physiological data collected by the system.

Figure 2:
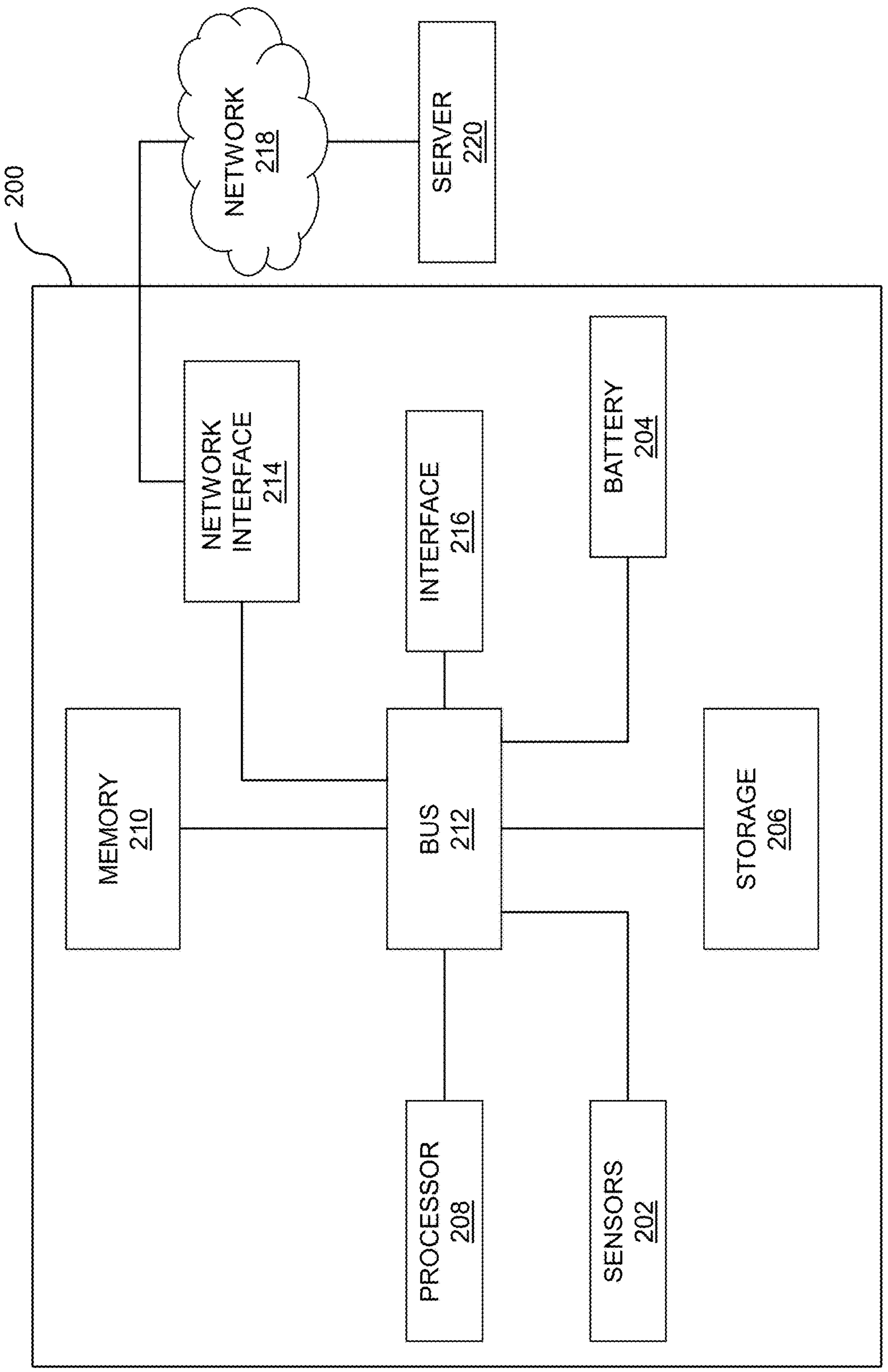
FIG. 2 shows a block diagram illustrating components of a wearable physiological measurement system configured to provide continuous collection and monitoring of physiological data.

FIG. 2 shows a block diagram illustrating exemplary components of a wearable physiological measurement system 200 configured to provide continuous collection and monitoring of physiological data. The wearable system 200 includes one or more sensors 202. As discussed above, the sensors 202 may include a heart rate monitor. In some embodiments, the wearable system 200 may further include one or more of sensors for detecting calorie burn, distance and activity. Calorie burn may be based on a user's heart rate, and a calorie burn measurement may be improved if a user chooses to provide his or her weight and/or other physical parameters. In some embodiments, manual entering of data is not required in order to derive calorie burn; however, data entry may be used to improve the accuracy of the results. In some embodiments, if a user has forgotten to enter a new weight, he/she can enter it for past weeks and the calorie burn may be updated accordingly.

The sensors 202 may include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance, whether it be in real terms as steps or miles or as a converted number. Activity sensors may be used, for example, to classify or categorize activity, such as walking, running, performing another sport, standing, sitting or lying down. In some embodiments, one or more of collected physiological data may be aggregated to generate an aggregate activity level. For example, heart rate, calorie burn, and distance may be used to derive an aggregate activity level. The aggregate level may be compared with or evaluated relative to previous recordings of the user's aggregate activity level, as well as the aggregate activity levels of other users.

The sensors 202 may include a thermometer for monitoring the user's body or skin temperature. In one embodiment, the sensors may be used to recognize sleep based on a temperature drop, GSR data, lack of activity according to data collected by the accelerometer, and reduced heart rate as measured by the heart rate monitor. The body temperature, in conjunction with heart rate monitoring and motion, may be used to interpret whether a user is sleeping or just resting, as body temperature drops significantly when an individual is about to fall asleep), and how well an individual is sleeping as motion indicates a lower quality of sleep. The body temperature may also be used to determine whether the user is exercising and to categorize and/or analyze activities.

The system 200 includes one or more batteries 204. According to one embodiment, the one or more batteries may be configured to allow continuous wear and usage of the wearable system. In one embodiment, the wearable system may include two or more batteries. The system may include a removable battery that may be recharged using a charger. In one example, the removable battery may be configured to slip in and out of a head portion of the system, attach onto the bracelet, or the like. In one example, the removable battery may be able to power the system for around a week. Additionally, the system may include a built-in battery. The built-in battery may be recharged by the removable battery. The built-in battery may be configured to power the bracelet for around a day on its own. When the more removable battery is being charged, the user does not need to remove the system and may continue collecting data using the built-in battery. In other embodiments, the two batteries may both be removable and rechargeable.

In some embodiments, the system 200 may include a battery that is a wireless rechargeable battery. For example, the battery may be recharged by placing the system or the battery on a rechargeable mat. In other example, the battery may be a long range wireless rechargeable battery. In other embodiments, the battery may be a rechargeable via motion. In yet other embodiments, the battery may be rechargeable using a solar energy source.

The wearable system 200 includes one or more non-transitory computer-readable media 206 for storing raw data detected by the sensors of the system and processed data calculated by a processing module of the system.

The system 200 includes a processor 208, a memory 210, a bus 212, a network interface 214, and an interface 216. The network interface 214 is configured to wirelessly communicate data to an external network 218. The network 218 may include any communication network through which computer systems may exchange data. For example, the network 218 may include, but is not limited to, the Internet, an intranet, a LAN (Local Area Network), a WAN (Wide Area Network), a MAN (Metropolitan Area Network), a wireless network, an optical network, and the like. To exchange data via the network 218, the system 200 and the network 218 may use various methods, protocols and standards including, but not limited to, token ring, Ethernet, wireless Ethernet, Bluetooth, TCP/IP, UDP, HTTP, FTP, SNMP, SMS, MMS, SS7, JSON, XML, REST, SOAP, CORBA, IIOP, RMI, DCOM and Web Services. To ensure data transfer is secure, the system 200 may transmit data via the network using a variety of security measures including, but not limited to, TSL, SSL and VPN.

Some embodiments of the wearable system may be configured to stream information wirelessly to a social network. In some embodiments, data streamed from a user's wearable system to an external network 218 may be accessed by the user via a website. The network interface may be configured such that data collected by the system may be streamed wirelessly. In some embodiments, data may be transmitted automatically, without the need to manually press any buttons. In some embodiments, the system may include a cellular chip built into the system. In one example, the network interface may be configured to stream data using Bluetooth technology. In another example, the network interface may be configured to stream data using a cellular data service, such as via a 3G or 4G cellular network.

The system 200 may be coupled to one or more servers 220 via a communication network 218.

In some embodiments, a physiological measurement system may be configured in a modular design to enable continuous operation of the system in monitoring physiological information of a user wearing the system. The module design may include a strap and a separate modular head portion or housing that is removably couplable to the strap.

In the non-limiting illustrative module design, the strap 102 of a physiological measurement system may be provided with a set of components that enables continuous monitoring of at least a heart rate of the user so that it is independent and fully self-sufficient in continuously monitoring the heart rate without requiring the modular head portion 104. In one embodiment, the strap includes a plurality of light emitters for emitting light toward the user's skin, a plurality of light detectors for receiving light reflected from the user's skin, an electronic circuit board comprising a plurality of electronic components configured for analyzing data corresponding to the reflected light to automatically and continually determine a heart rate of the user, and a first set of one or more batteries for supplying electrical power to the light emitters, the light detectors and the electronic circuit board. In some embodiments, the strap may also detect one or more other physiological characteristics of the user including, but not limited to, temperature, galvanic skin response, and the like.

Certain exemplary systems may be configured to be coupled to any desired part of a user's body so that the system may be moved from one portion of the body (e.g., wrist) to another portion of the body (e.g., ankle) without affecting its function and operation. In one embodiment, the identity of the portion of the user's body to which the wearable system is attached may be determined based on one or more parameters including, but not limited to, absorbance level of light as returned from the user's skin, reflectance level of light as returned from the user's skin, motion sensor data (e.g., accelerometer and/or gyroscope), altitude of the wearable system, and the like.

In some embodiments, the processing module is configured to determine that the wearable system is taken off from the user's body. In one example, the processing module may determine that the wearable system has been taken off if data from the galvanic skin response sensor indicates data atypical of a user's skin. If the wearable system is determined to be taken off from the user's body, the processing module is configured to deactivate the light emitters and the light detectors and cease monitoring of the heart rate of the user to conserve power.

Exemplary systems include a processing module configured to filter the raw photoplethysmography data received from the light detectors to minimize contributions due to motion, and subsequently process the filtered data to detect peaks in the data that correspond with heart beats of a user. The overall algorithm for detecting heart beats takes as input the analog signals from optical sensors (mV) and accelerometer, and outputs an implied beats per minute (heart rate) of the signal accurate within a few beats per minute as that determined by an electrocardiography machine even during motion.

In one aspect, using multiple LEDs with different wavelengths reacting to movement in different ways can allow for signal recovery with standard signal processing techniques. The availability of accelerometer information can also be used to compensate for coarse movement signal corruption. In order to increase the range of movements that the algorithm can successfully filter out, an aspect utilizes techniques that augment the algorithm already in place. For example, filtering violent movements of the arm during very short periods of time, such as boxing as exercising, may be utilized by the system. By selective sampling and interpolating over these impulses, an aspect can account for more extreme cases of motion. Additionally, an investigation into different LED wavelengths, intensities, and configurations can allow the systems described herein to extract a signal across a wide spectrum of skin types and wrist sizes. In other words, motion filtering algorithms and signal processing techniques may assist in mitigating the risk caused by movement.

Figure 3:
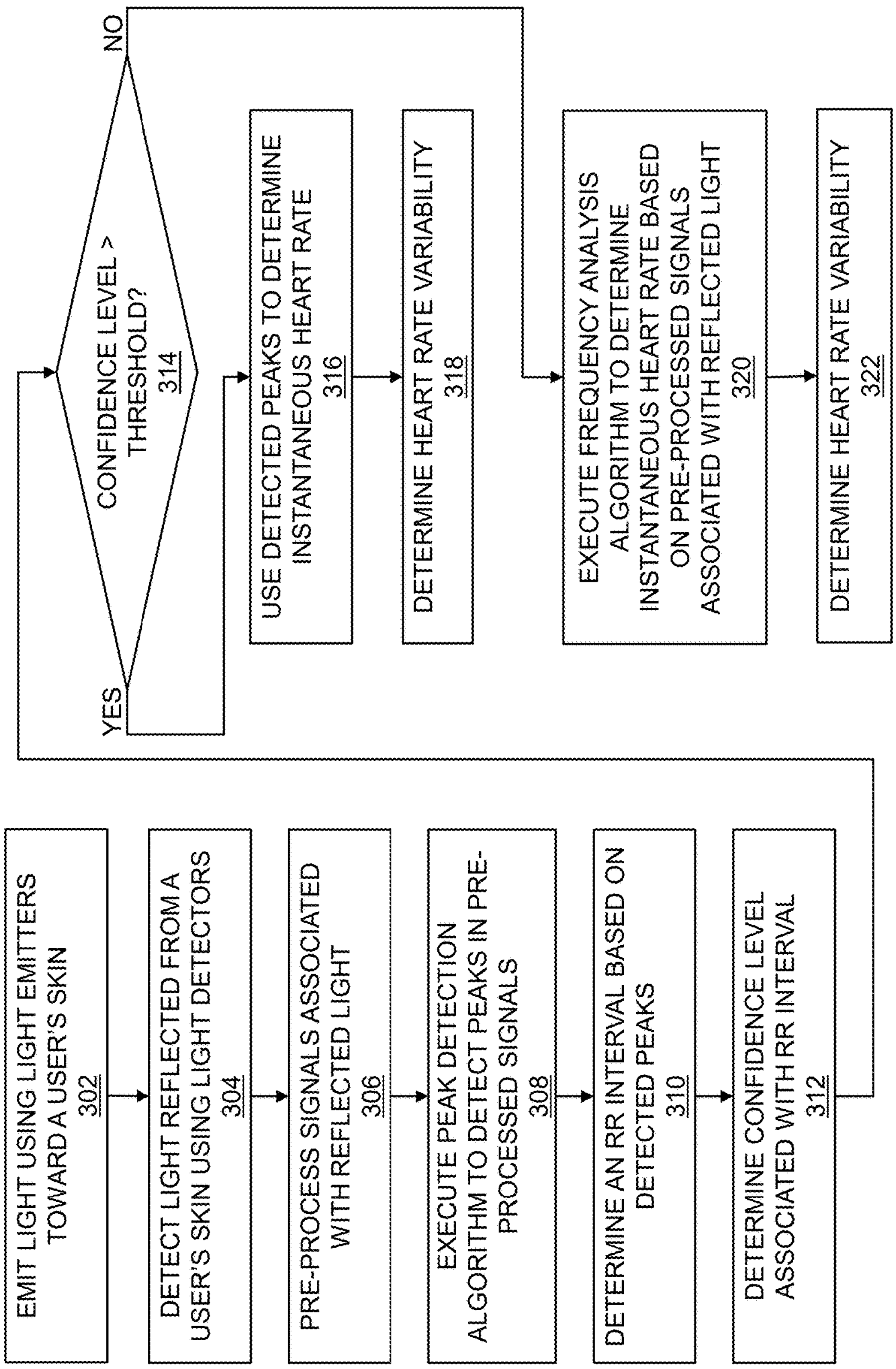
FIG. 3 is a flowchart illustrating a signal processing algorithm for generating a sequence of heart rates for every detected heartbeat that may be embodied in computer-executable instructions stored on one or more non-transitory computer-readable media.

FIG. 3 is a flowchart illustrating an exemplary signal processing algorithm for generating a sequence of heart rates for every detected heartbeat that is embodied in computer-executable instructions stored on one or more non-transitory computer-readable media. In step 302, light emitters of a wearable physiological measurement system emit light toward a user's skin. In step 304, light reflected from the user's skin is detected at the light detectors in the system. In step 306, signals or data associated with the reflected light are pre-processed using any suitable technique to facilitate detection of heart beats. In step 308, a processing module of the system executes one or more computer-executable instructions associated with a peak detection algorithm to process data corresponding to the reflected light to detect a plurality of peaks associated with a plurality of beats of the user's heart. In step 310, the processing module determines an RR interval based on the plurality of peaks detected by the peak detection algorithm. In step 312, the processing module determines a confidence level associated with the RR interval.

Based on the confidence level associated with the RR interval estimate, the processing module selects either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, an implementation maintains the ability to obtain the RR intervals for as long as possible, even in the case of motion, thereby maximizing the information that can be extracted.

For example, in step 314, it is determined whether the confidence level associated with the RR interval is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, in step 316, the processing module may use the plurality of peaks to determine an instantaneous heart rate of the user. On the other hand, in step 320, based on a determination that the confidence level associated with the RR interval is equal to or below the predetermined threshold, the processing module may execute one or more computer-executable instructions associated with the frequency analysis algorithm to determine an instantaneous heart rate of the user. The confidence threshold may be dynamically set based on previous confidence levels.

In some embodiments, in steps 318 or 322, the processing module determines a heart rate variability of the user based on the sequence of the instantaneous heart rates/beats.

The system may include a display device configured to render a user interface for displaying the sequence of the instantaneous heart rates of the user, the RR intervals and/or the heart rate variability determined by the processing module. The system may include a storage device configured to store the sequence of the instantaneous heart rates, the RR intervals and/or the heart rate variability determined by the processing module.

In one aspect, the system may switch between different analytical techniques for determining a heart rate such as a statistical technique for detecting a heart rate and a frequency domain technique for detecting a heart rate. These two different modes have different advantages in terms of accuracy, processing efficiency, and information content, and as such may be useful at different times and under different conditions. Rather than selecting one such mode or technique as an attempted optimization, the system may usefully switch back and forth between these differing techniques, or other analytical techniques, using a predetermined criterion. An exemplary statistical technique employs probabilistic peak detection. An exemplary frequency analysis algorithm used in an implementation isolates the highest frequency components of the optical data, checks for harmonics common in both the accelerometer data and the optical data, and performs filtering of the optical data. This latter algorithm may, for example, take as input raw analog signals from the accelerometer (3-axis) and pulse sensors, and output heart rate values or beats per minute (BPM) for a given period of time related to the window of the spectrogram.

The exemplary wearable system computes heart rate variability (HRV) to obtain an understanding of the recovery status of the body. These values are captured right before a user awakes or when the user is not moving, in both cases photoplethysmography (PPG) variability yielding equivalence to the ECG HRV. HRV is traditionally measured using an ECG machine and obtaining a time series of R-R intervals. Because an exemplary wearable system utilizes photoplethysmography (PPG), it does not obtain the electric signature from the heart beats; instead, the peaks in the obtained signal correspond to arterial blood volume. At rest, these peaks are directly correlated with cardiac cycles, which enables the calculation of HRV via analyzing peak-to-peak intervals (the PPG analog of RR intervals). It has been demonstrated in medical literature that these peak-to-peak intervals, the "PPG variability," is identical to ECG HRV while at rest.

An exemplary system may include a processing module that is configured to automatically adjust one or more operational characteristics of the light emitters and/or the light detectors to minimize power consumption while ensuring that all heart beats of the user are reliably and continuously detected. The operational characteristics may include, but are not limited to, a frequency of light emitted by the light emitters, the number of light emitters activated, a duty cycle of the light emitters, a brightness of the light emitters, a sampling rate of the light detectors, and the like. The processing module may adjust the operational characteristics based on one or more signals or indicators obtained or derived from one or more sensors in the system including, but not limited to, a motion status of the user, a sleep status of the user, historical information on the user's physiological and/or habits, an environmental or contextual condition (e.g., ambient light conditions), a physical characteristic of the user (e.g., the optical characteristics of the user's skin), and the like.

In one embodiment, the processing module may receive data on the motion of the user using, for example, an accelerometer. The processing module may process the motion data to determine a motion status of the user which indicates the level of motion of the user, for example, exercise, light motion (e.g., walking), no motion or rest, sleep, and the like. The processing module may adjust the duty cycle of one or more light emitters and the corresponding sampling rate of the one or more light detectors based on the motion status. For example, light emitters for PPG may be activated at a duty cycle ranging from about 1% to about 100%. In another example, the light emitters may be activated at a duty cycle ranging from about 20% to about 50% to minimize power consumption. Certain exemplary sampling rates of the light detectors may range from about 50 Hz to about 1000 Hz, but are not limited to these exemplary rates. Certain non-limiting sampling rates are, for example, about 100 Hz, 200 Hz, 500 Hz, and the like.

In one non-limiting example, the light detectors may sample continuously when the user is performing an exercise routine so that the error standard deviation is kept within 5 beats per minute (BPM). When the user is at rest, the light detectors may be activated for about a 1% duty cycle-10 milliseconds each second (i.e., 1% of the time) so that the error standard deviation is kept within 5 BPM (including an error standard deviation in the heart rate measurement of 2 BPM and an error standard deviation in the heart rate changes between measurement of 3 BPM). When the user is in light motion (e.g., walking), the light detectors may be activated for about a 10% duty cycle-100 milliseconds each second (i.e., 10% of the time) so that the error standard deviation is kept within 6 BPM (including an error standard deviation in the heart rate measurement of 2 BPM and an error standard deviation in the heart rate changes between measurement of 4 BPM).

The processing module may adjust the brightness of one or more light emitters by adjusting the current supplied to the light emitters. For example, a first level of brightness may be set by current ranging between about 1 mA to about 10 mA, but is not limited to this exemplary range. A second higher level of brightness may be set by current ranging from about 11 mA to about 30 mA, but is not limited to this exemplary range. A third higher level of brightness may be set by current ranging from about 80 mA to about 120 mA, but is not limited to this exemplary range. In one non-limiting example, first, second and third levels of brightness may be set by current of about 5 mA, about 20 mA and about 100 mA, respectively.

Shorter-wavelength LEDs may require more power than is required by other types of heart rate sensors, such as, a piezo-sensor or an infrared sensor. Therefore, an exemplary wearable system may provide and use a unique combination of sensors-one or more light detectors for periods where motion is expected and one or more piezo and/or infrared sensors for low motion periods (e.g., sleep)—to save battery life. Certain other embodiments of a wearable system may exclude piezo-sensors and/or infrared sensors.

For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), non-light based sensors may be activated. The threshold levels of motion that trigger adjustment of the type of sensor may be based on one or more factors including, but are not limited to, skin properties, ambient light conditions, and the like.

The system may determine the type of sensor to use at a given time based on the level of motion (e.g., via an accelerometer) and whether the user is asleep (e.g., based on movement input, skin temperature and heart rate). Based on a combination of these factors the system selectively chooses which type of sensor to use in monitoring the heart rate of the user. Common symptoms of being asleep are periods of no movement or small bursts of movement (such as shifting in bed), lower skin temperature (although it is not a dramatic drop from normal), drastic GSR changes, and heart rate that is below the typical resting heart rate when the user is awake. These variables depend on the physiology of a person and thus a machine learning algorithm is trained with user-specific input to determine when he/she is awake/asleep and determine from that the exact parameters that cause the algorithm to deem someone asleep.

In an exemplary configuration, the light detectors may be positioned on the underside of the wearable system and all of the heart rate sensors may be positioned adjacent to each other. For example, the low power sensor(s) may be adjacent to the high power sensor(s) as the sensors may be chosen and placed where the strongest signal occurs. In one example configuration, a 3-axis accelerometer may be used that is located on the top part of the wearable system. In some embodiments, an operational characteristic of the microprocessor may be automatically adjusted to minimize power consumption. This adjustment may be based on a level of motion of the user's body.

More generally, the above description contemplates a variety of techniques for sensing conditions relating to heart rate monitoring or related physiological activity either directly (e.g., confidence levels or accuracy of calculated heart rate) or indirectly (e.g., motion detection, temperature). However measured, these sensed conditions can be used to intelligently select from among a number of different modes, including hardware modes, software modes, and combinations of the foregoing, for monitoring heart rate based on, e.g., accuracy, power usage, detected activity states, and so forth. Thus there is disclosed herein techniques for selecting from among two or more different heart rate monitoring modes according to a sensed condition.

Exemplary embodiments provide an analytics system for providing qualitative and quantitative monitoring of a user's body, health and physical training. The analytics system is implemented in computer-executable instructions encoded on one or more non-transitory computer-readable media. The analytics system relies on and uses continuous data on one or more physiological parameters including, but not limited to, heart rate. The continuous data used by the analytics system may be obtained or derived from an exemplary physiological measurement system disclosed herein, or may be obtained or derived from a derived source or system, for example, a database of physiological data. In some embodiments, the analytics system computes, stores and displays one or more indicators or scores relating to the user's body, health and physical training including, but not limited to, an intensity score and a recovery score. The scores may be updated in real-time and continuously or at specific time periods, for example, the recovery score may be determined every morning upon waking up, the intensity score may be determined in real-time or after a workout routine or for an entire day.

In certain exemplary embodiments, a fitness score may be automatically determined based on the physiological data of two or more users of exemplary wearable systems.

An intensity score or indicator provides an accurate indication of the cardiovascular intensities experienced by the user during a portion of a day, during the entire day or during any desired period of time (e.g., during a week or month). The intensity score is customized and adapted for the unique physiological properties of the user and takes into account, for example, the user's age, gender, anaerobic threshold, resting heart rate, maximum heart rate, and the like. If determined for an exercise routine, the intensity score provides an indication of the cardiovascular intensities experienced by the user continuously throughout the routine. If determined for a period of including and beyond an exercise routine, the intensity score provides an indication of the cardiovascular intensities experienced by the user during the routine and also the activities the user performed after the routine (e.g., resting on the couch, active day of shopping) that may affect their recovery or exercise readiness.

Figure 4:
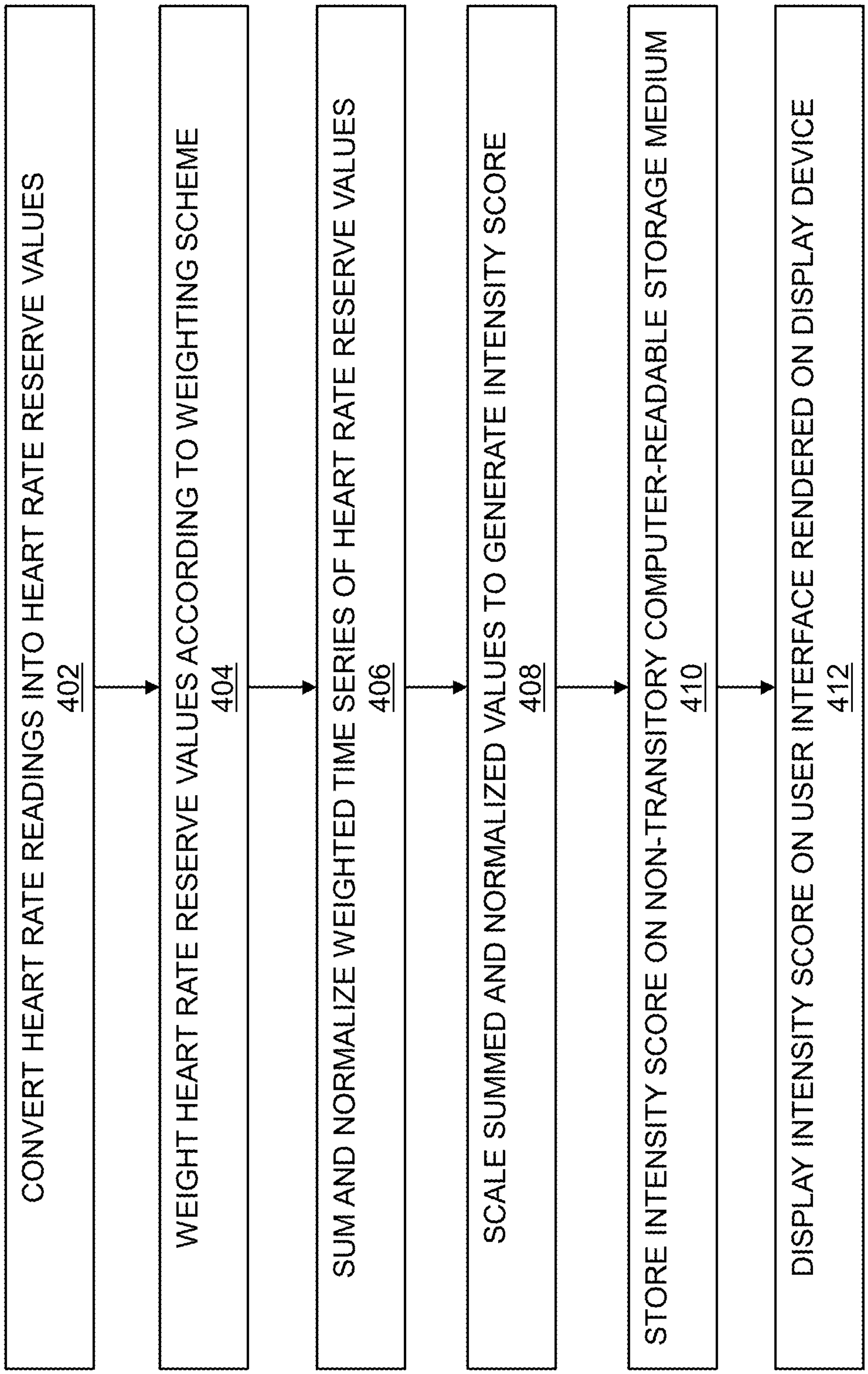
FIG. 4 is a flowchart illustrating a method of determining an intensity score.

In exemplary embodiments, the intensity score is calculated based on the user's heart rate reserve (HRR) as detected continuously throughout the desired time period, for example, throughout the entire day. In one embodiment, the intensity score is an integral sum of the weighted HRR detected continuously throughout the desired time period. FIG. 4 is a flowchart illustrating an exemplary method of determining an intensity score.

In step 402, continuous heart rate readings are converted to HRR values. A time series of heart rate data used in step 402 may be denoted as:

$$H \in T$$

A time series of HRR measurements, v(t), may be defined in the following expression in which MHR is the maximum heart rate and RHR is the resting heart rate of the user:

$$v(t) = \frac{H(t) - RHR}{MHR - RHR}$$

In step 404, the HRR values are weighted according to a suitable weighting scheme. Cardiovascular intensity, indicated by an intensity score, is defined in the following expression in which w is a weighting function of the HRR measurements:

$$I(t_o, t_1) = \int_{t_0}^{t_1} w(v(t))dt$$

In step 406, the weighted time series of HRR values is summed and normalized.

$$I_t = \int_T w(v(t))dt \le w(1)|T|$$

This, the weighted sum is normalized to the unit interval, i.e., [0, 1]

$$N_T = \frac{I_T}{w(1) \cdot 24 \text{ hr}}$$

In step 408, the summed and normalized values are scaled to generate user-friendly intensity score values. That is, the unit interval is transformed to have any desired distribution in a scale (e.g., a scale including 21 points from 0 to 21), for example, arctangent, sigmoid, sinusoidal, and the like. In certain distributions, the intensity values increase at a linear rate along the scale, and in others, at the highest ranges the intensity values increase at more than a linear rate to indicate that it is more difficult to climb in the scale toward the extreme end of the scale. In some embodiments, the raw intensity scores are scaled by fitting a curve to a selected group of "canonical" exercise routines that are predefined to have particular intensity scores.

In one embodiment, monotonic transformations of the unit interval are achieved to transform the raw HRR values to user-friendly intensity scores. An exemplary scaling scheme, expressed as $f: [0, 1] \rightarrow [0, 1]$, is performed using the following function:

$$(x, N, p) = 0.5\left(\frac{\arctan(N(x-p))}{\pi/2} + 1\right)$$

To generate an intensity score, the resulting value may be multiplied by a number based on the desired scale of the intensity score. For example, if the intensity score is graduated from zero to 21, then the value may be multiplied by 21.

In step 410, the intensity score values are stored on a non-transitory storage medium for retrieval, display and usage. In step 412, the intensity score values are, in some embodiments, displayed on a user interface rendered on a visual display device. The intensity score values may be displayed as numbers and/or with the aid of graphical tools, e.g., a graphical display of the scale of intensity scores with current score, and the like. In some embodiments, the intensity score may be indicated by audio. In step 412, the intensity score values are, in some embodiments, displayed along with one or more quantitative or qualitative pieces of information on the user including, but not limited to, whether the user has exceeded his/her anaerobic threshold, the heart rate zones experienced by the user during an exercise routine, how difficult an exercise routine was in the context of the user's training, the user's perceived exertion during an exercise routine, whether the exercise regimen of the user should be automatically adjusted (e.g., made easier if the intensity scores are consistently high), whether the user is likely to experience soreness the next day and the level of expected soreness, characteristics of the exercise routine (e.g., how difficult it was for the user, whether the exercise was in bursts or activity, whether the exercise was tapering, etc.), and the like. In one embodiment, the analytics system may automatically generate, store and display an exercise regimen customized based on the intensity scores of the user.

Step 406 may use any of a number of exemplary static or dynamic weighting schemes that enable the intensity score to be customized and adapted for the unique physiological properties of the user. In one exemplary static weighting scheme, the weights applied to the HRR values are based on static models of a physiological process. The human body employs different sources of energy with varying efficiencies and advantages at different HRR levels. For example, at the anaerobic threshold (AT), the body shifts to anaerobic respiration in which the cells produce two adenosine triphosphate (ATP) molecules per glucose molecule, as opposed to 36 at lower HRR levels. At even higher HRR levels, there is a further subsequent threshold (CPT) at which creatine triphosphate (CTP) is employed for respiration with even less efficiency.

In order to account for the differing levels of cardiovascular exertion and efficiency at the different HRR levels, in one embodiment, the possible values of HRR are divided into a plurality of categories, sections or levels (e.g., three) dependent on the efficiency of cellular respiration at the respective categories. The HRR parameter range may be divided in any suitable manner, such as, piecewise, including piecewise-linear, piecewise-exponential, and the like. An exemplary piecewise-linear division of the HRR parameter range enables weighting each category with strictly increasing values. This scheme captures an accurate indication of the cardiovascular intensity experienced by the user because it is more difficult to spend time at higher HRR values, which suggests that the weighting function should increase at the increasing weight categories.

In one non-limiting example, the HRR parameter range may be considered a range from zero (0) to one (1) and divided into categories with strictly increasing weights. In one example, the HRR parameter range may be divided into a first category of a zero HRR value and may assign this category a weight of zero; a second category of HRR values falling between zero (0) and the user's anaerobic threshold (AT) and may assign this category a weight of one (1); a third category of HRR values falling between the user's anaerobic threshold (AT) and a threshold at which the user's body employs creatine triphosphate for respiration (CPT) and may assign this category a weight of 18; and a fourth category of HRR values falling between the creatine triphosphate threshold (CPT) and one (1) and may assign this category a weight of 42, although other numbers of HRR categories and different weight values are possible. That is, in this example, the weights are defined as:

$$w(v) = \begin{cases} 0: v = 0 \\ 1: v \in (0, AT] \\ 18: v \in (AT, CPT] \\ 42: v \in (CPT, 1] \end{cases}$$

In another exemplary embodiment of the weighting scheme, the HRR time series is weighted iteratively based on the intensity scores determined thus far (e.g., the intensity score accrued thus far) and the path taken by the HRR values to get to the present intensity score. In another exemplary embodiment of the weighting scheme, a predictive approach is used by modeling the weights or coefficients to be the coefficient estimates of a logistic regression model. One of ordinary skill in the art will recognize that two or more aspects of any of the disclosed weighting schemes may be applied separately or in combination in an exemplary method for determining an intensity score.

In one aspect, heart rate zones quantify the intensity of workouts by weighing and comparing different levels of heart activity as percentages of maximum heart rate. Analysis of the amount of time an individual spends training at a certain percentage of his/her MHR may reveal his/her state of physical exertion during a workout. This intensity, developed from the heart rate zone analysis, motion, and activity, may then indicate his/her need for rest and recovery after the workout, e.g., to minimize delayed onset muscle soreness (DOMS) and prepare him/her for further activity. As discussed above, MHR, heart rate zones, time spent above the anaerobic threshold, and HRV in RSA (Respiratory Sinus Arrhythmia) regions—as well as personal information (gender, age, height, weight, etc.) may be utilized in data processing.

A recovery score or indicator provides an accurate indication of the level of recovery of a user's body and health after a period of physical exertion. The human autonomic nervous system controls the involuntary aspects of the body's physiology and is typically subdivided into two branches: parasympathetic (deactivating) and sympathetic (activating). Heart rate variability (HRV), i.e., the fluctuation in inter-heartbeat interval time, is a commonly studied result of the interplay between these two competing branches. Parasympathetic activation reflects inputs from internal organs, causing a decrease in heart rate. Sympathetic activation increases in response to stress, exercise and disease, causing an increase in heart rate. For example, when high intensity exercise takes place, the sympathetic response to the exercise persists long after the completion of the exercise. When high intensity exercise is followed by insufficient recovery, this imbalance lasts typically until the next morning, resulting in a low morning HRV. This result should be taken as a warning sign as it indicates that the parasympathetic system was suppressed throughout the night. While suppressed, normal repair and maintenance processes that ordinarily would occur during sleep were suppressed as well. Suppression of the normal repair and maintenance processes results in an unprepared state for the next day, making subsequent exercise attempts more challenging.

The recovery score is customized and adapted for the unique physiological properties of the user and takes into account, for example, the user's heart rate variability (HRV), resting heart rate, sleep quality and recent physiological strain (indicated, in one example, by the intensity score of the user). In one exemplary embodiment, the recovery score is a weighted combination of the user's heart rate variability (HRV), resting heart rate, sleep quality indicated by a sleep score, and recent strain (indicated, in one example, by the intensity score of the user). In an exemplar, the sleep score combined with performance readiness measures (such as, morning heart rate and morning heart rate variability) provides a complete overview of recovery to the user. By considering sleep and HRV alone or in combination, the user can understand how exercise-ready he/she is each day and to understand how he/she arrived at the exercise-readiness score each day, for example, whether a low exercise-readiness score is a predictor of poor recovery habits or an inappropriate training schedule. This insight aids the user in adjusting his/her daily activities, exercise regimen and sleeping schedule therefore obtain the most out of his/her training.

In some cases, the recovery score may take into account perceived psychological strain experienced by the user. In some cases, perceived psychological strain may be detected from user input via, for example, a questionnaire on a mobile device or web application. In other cases, psychological strain may be determined automatically by detecting changes in sympathetic activation based on one or more parameters including, but not limited to, heart rate variability, heart rate, galvanic skin response, and the like.

With regard to the user's HRV used in determining the recovery score, suitable techniques for analyzing HRV include, but are not limited to, time-domain methods, frequency-domain methods, geometric methods and non-linear methods. In one embodiment, the HRV metric of the root-mean-square of successive differences (RMSSD) of RR intervals is used. The analytics system may consider the magnitude of the differences between 7-day moving averages and 3-day moving averages of these readings for a given day. Other embodiments may use Poincaré Plot analysis or other suitable metrics of HRV.

The recovery score algorithm may take into account RHR along with history of past intensity and recovery scores.

With regard to the user's resting heart rate, moving averages of the resting heart rate are analyzed to determine significant deviations. Consideration of the moving averages is important since day-to-day physiological variation is quite large even in healthy individuals. Therefore, the analytics system may perform a smoothing operation to distinguish changes from normal fluctuations.

Although an inactive condition, sleep is a highly active recovery state during which a major portion of the physiological recovery process takes place. Nonetheless, a small, yet significant, amount of recovery can occur throughout the day by rehydration, macronutrient replacement, lactic acid removal, glycogen re-synthesis, growth hormone production and a limited amount of musculoskeletal repair. In assessing the user's sleep quality, the analytics system generates a sleep score using continuous data collected by an exemplary physiological measurement system regarding the user's heart rate, skin conductivity, ambient temperature and accelerometer/gyroscope data throughout the user's sleep. Collection and use of these four streams of data enable an understanding of sleep previously only accessible through invasive and disruptive over-night laboratory testing. For example, an increase in skin conductivity when ambient temperature is not increasing, the wearer's heart rate is low, and the accelerometer/gyroscope shows little motion, may indicate that the wearer has fallen asleep. The sleep score indicates and is a measure of sleep efficiency (how good the user's sleep was) and sleep duration (if the user had sufficient sleep). Each of these measures is determined by a combination of physiological parameters, personal habits and daily stress/strain (intensity) inputs. The actual data measuring the time spent in various stages of sleep may be combined with the wearer's recent daily history and a longer-term data set describing the wearer's personal habits to assess the level of sleep sufficiency achieved by the user. The sleep score is designed to model sleep quality in the context of sleep duration and history. It thus takes advantage of the continuous monitoring nature of the exemplary physiological measurement systems disclosed herein by considering each sleep period in the context of biologically-determined sleep needs, pattern-determined sleep needs and historically-determined sleep debt.

The recovery and sleep score values are stored on a non-transitory storage medium for retrieval, display and usage. The recovery and/or sleep score values are, in some embodiments, displayed on a user interface rendered on a visual display device. The recovery and/or sleep score values may be displayed as numbers and/or with the aid of graphical tools, e.g., a graphical display of the scale of recovery scores with current score, and the like. In some embodiments, the recovery and/or sleep score may be indicated by audio. The recovery score values are, in some embodiments, displayed along with one or more quantitative or qualitative pieces of information on the user including, but not limited to, whether the user has recovered sufficiently, what level of activity the user is prepared to perform, whether the user is prepared to perform an exercise routine a particular desired intensity, whether the user should rest and the duration of recommended rest, whether the exercise regimen of the user should be automatically adjusted (e.g., made easier if the recovery score is low), and the like. In one embodiment, the analytics system may automatically generate, store and display an exercise regimen customized based on the recovery scores of the user alone or in combination with the intensity scores.

As discussed above, the sleep performance metric may be based on parameters like the number of hours of sleep, sleep onset latency, and the number of sleep disturbances. In this manner, the score may compare a tactical athlete's duration and quality of sleep in relation to the tactical athlete's evolving sleep need (e.g., a number of hours based on recent strain, habitual sleep need, signs of sickness, and sleep debt). By way of example, a soldier may have a dynamically changing need for sleep, and it may be important to consider the total hours of sleep in relation to the amount of sleep that may have been required. By providing an accurate sensor for sleep and sleep performance, an aspect may evaluate sleep in the context of the overall day and lifestyle of a specific user.

Figure 5:
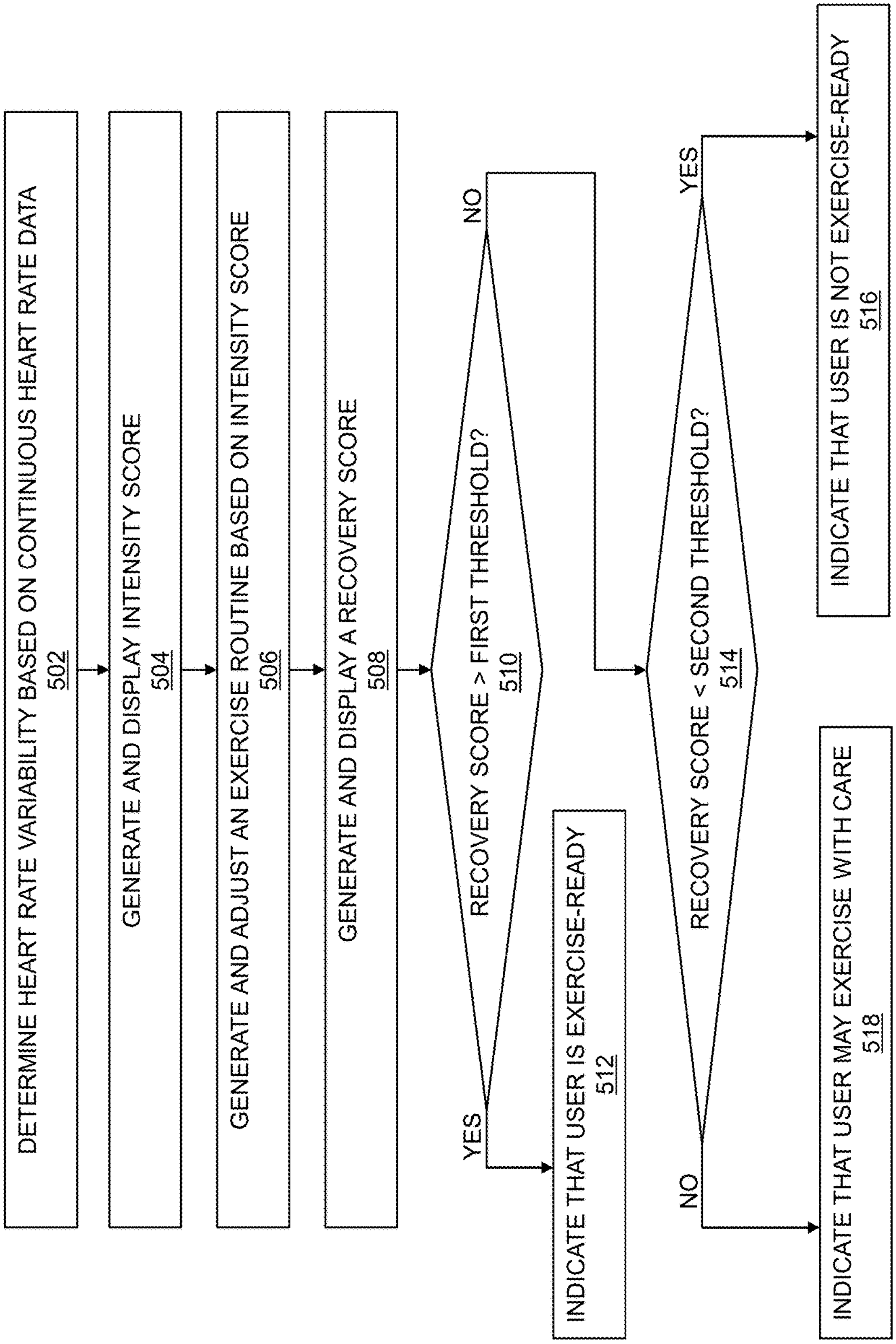
FIG. 5 is a flowchart illustrating a method by which a user may use intensity and recovery scores.

FIG. 5 is a flowchart illustrating an exemplary method by which a user may use intensity and recovery scores. In step 502, the wearable physiological measurement system begins determining heart rate variability (HRV) measurements based on continuous heart rate data collected by an exemplary physiological measurement system. In some cases, it may take the collection of several days of heart rate data to obtain an accurate baseline for the HRV. In step 504, the analytics system may generate and display intensity score for an entire day or an exercise routine. In some cases, the analytics system may display quantitative and/or qualitative information corresponding to the intensity score.

In step 506, in an exemplary embodiment, the analytics system may automatically generate or adjust an exercise routine or regimen based on the user's actual intensity scores or desired intensity scores. For example, based on inputs of the user's actual intensity scores, a desired intensity score (that is higher than the actual intensity scores) and a first exercise routine currently performed by the user (e.g., walking), the analytics system may recommend a second different exercise routine that is typically associated with higher intensity scores than the first exercise routine (e.g., running).

In step 508, at any given time during the day (e.g., every morning), the analytics system may generate and display a recovery score. In some cases, the analytics system may display quantitative and/or qualitative information corresponding to the intensity score. For example, in step 510, in an exemplary embodiment, the analytics system may determine if the recovery is greater than (or equal to or greater than) a first predetermined threshold (e.g., about 60% to about 80% in some examples) that indicates that the user is recovered and is ready for exercise. If this is the case, in step 512, the analytics system may indicate that the user is ready to perform an exercise routine at a desired intensity or that the user is ready to perform an exercise routine more challenging than the past day's routine. Otherwise, in step 514, the analytics system may determine if the recovery is lower than (or equal to or lower than) a second predetermined threshold (e.g., about 10% to about 40% in some examples) that indicates that the user has not recovered. If this is the case, in step 516, the analytics system may indicate that the user should not exercise and should rest for an extended period. The analytics system may, in some cases, the duration of recommended rest. Otherwise, in step 518, the analytics system may indicate that the user may exercise according to his/her exercise regimen while being careful not to overexert him/herself. The thresholds may, in some cases, be adjusted based on a desired intensity at which the user desires to exercise. For example, the thresholds may be increased for higher planned intensity scores.

Figure 6:
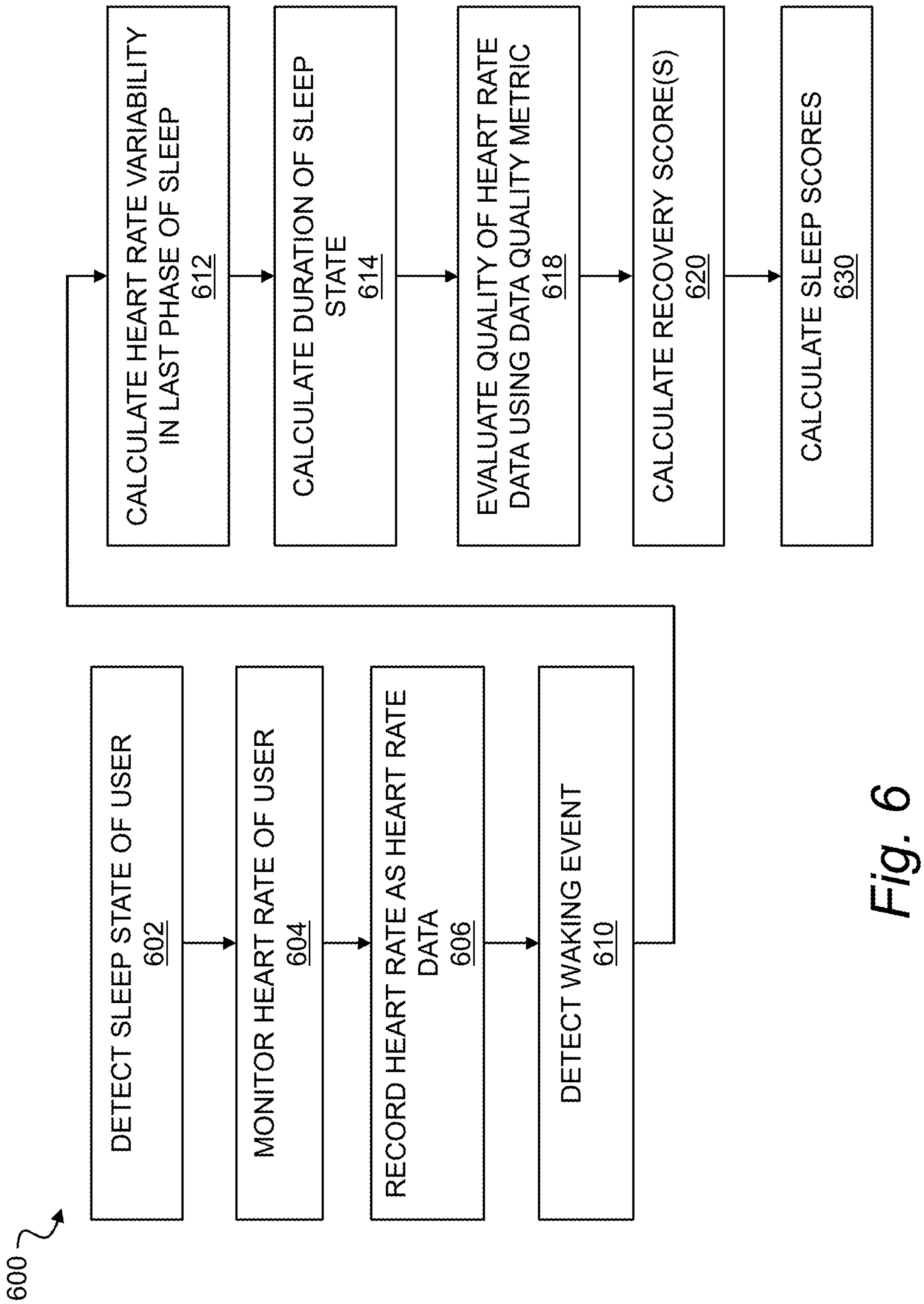
FIG. 6 is a flow chart illustrating a method for detecting heart rate variability in sleep states.

FIG. 6 is a flow chart illustrating a method for detecting heart rate variability in sleep states. The method 600 may be used in cooperation with any of the devices, systems, and methods described herein, such as by operating a wearable, continuous physiological monitoring device to perform the following steps. The wearable, continuous physiological monitoring system may for example include a processor, one or more light emitting diodes, one or more light detectors configured to obtain heart rate data from a user, and one or more other sensors to assist in detecting stages of sleep. In general, the method 600 aims to measure heart rate variability in the last phase of sleep before waking in order to provide a consistent and accurate basis for calculating a physical recovery score.

As shown in step 602, the method 600 may include detecting a sleep state of a user. This may, for example, include any form of continuous or periodic monitoring of sleep states using any of a variety of sensors or algorithms as generally described herein.

Sleep states (also be referred to as "sleep phases," "sleep cycles," "sleep stages," or the like) may include rapid eye movement (REM) sleep, non-REM sleep, or any states/stages included therein. The sleep states may include different phases of non-REM sleep, including Stages 1-3. Stage 1 of non-REM sleep generally includes a state where a person's eyes are closed, but the person can be easily awakened; Stage 2 of non-REM sleep generally includes a state where a person is in light sleep, i.e., where the person's heart rate slows and their body temperature drops in preparation for deeper sleep; and Stage 3 of non-REM sleep generally includes a state of deep sleep, where a person is not easily awakened. Stage 3 is often referred to as delta sleep, deep sleep, or slow wave sleep (i.e., from the high amplitude but small frequency brain waves typically found in this stage). Slow wave sleep is thought to be the most restful form of sleep, which relieves subjective feelings of sleepiness and restores the body.

REM sleep on the other hand typically occurs 1-2 hours after falling asleep. REM sleep may include different periods, stages, or phases, all of which may be included within the sleep states that are detected as described herein. During REM sleep, breathing may become more rapid, irregular and shallow, eyes may jerk rapidly (thus the term "Rapid Eye Movement" or "REM"), and limb muscles may be temporarily paralyzed. Brain waves during this stage typically increase to levels experienced when a person is awake. Also, heart rate, cardiac pressure, cardiac output, and arterial pressure may become irregular when the body moves into REM sleep. This is the sleep state in which most dreams occur, and, if awoken during REM sleep, a person can typically remember the dreams. Most people experience three to five intervals of REM sleep each night.

Homeostasis is the balance between sleeping and waking, and having proper homeostasis may be beneficial to a person's health. Lack of sleep is commonly referred to as sleep deprivation, which tends to cause slower brain waves, a shorter attention span, heightened anxiety, impaired memory, mood disorders, and general mental, emotional, and physical fatigue. Sleep debt (the effect of not getting enough sleep) may result in the diminished abilities to perform high-level cognitive functions. A person's circadian rhythms (i.e., biological processes that display an endogenous, entrainable oscillation of about 24 hours) may be a factor in a person's optimal amount of sleep. Thus, sleep may in general be usefully monitored as a proxy for physical recovery. However, a person's heart rate variability at a particular moment during sleep—during the last phase of sleep preceding a waking event—can further provide an accurate and consistent basis for objectively calculating a recovery score following a period of sleep.

According to the foregoing, sleep of a user may be monitored to detect various sleep states, transitions, and other sleep-related information. For example, the device may monitor/detect the duration of sleep states, the transitions between sleep states, the number of sleep cycles or particular states, the number of transitions, the number of waking events, the transitions to an awake state, and so forth. Sleep states may be monitored and detected using a variety of strategies and sensor configurations according to the underlying physiological phenomena. For example, body temperature may be usefully correlated to various sleep states and transitions. Similarly, galvanic skin response may be correlated to sweating activity and various sleep states, any of which may also be monitored, e.g., with a galvanic skin response sensor, to determine sleep states. Physical motion can also be easily monitored using accelerometers or the like, which can be used to detect waking or other activity involving physical motion. In another aspect, heart rate activity itself may be used to infer various sleep states and transitions, either alone or in combination with other sensor data. Other sensors may also or instead be used to monitor sleep activity, such as brain wave monitors, pupil monitors, and so forth, although the ability to incorporate these types of detection into a continuously wearable physiological monitoring device may be somewhat limited depending on the contemplated configuration.

As shown in step 604, the method 600 may include monitoring a heart rate of the user substantially continuously with the continuous physiological monitoring system. Continuous heart rate monitoring is described above in significant detail, and the description is not repeated here except to note generally that this may include raw sensor data, heart rate data or peak data, and heart rate variability data over some historical period that can be subsequently correlated to various sleep states and activities.

As shown in step 606, the method 600 may include recording the heart rate as heart rate data. This may include storing the heart rate data in any raw or processed form on the device, or transmitting the data to a local or remote location for storage. In one aspect, the data may be stored as peak-to-peak data or in some other semi-processed form without calculating heart rate variability. This may be useful as a technique for conserving processing resources in a variety of contexts, for example where only the heart rate variability at a particular time is of interest. Data may be logged in some unprocessed or semi-processed form, and then the heart rate variability at a particular point in time can be calculated once the relevant point in time has been identified.

As shown in step 610, the method 600 may include detecting a waking event at a transition from the sleep state of the user to an awake state. It should be appreciated that the waking event may be a result of a natural termination of sleep, e.g., after a full night's rest, or in response to an external stimulus that causes awakening prior to completion of a natural sleep cycle. Regardless of the precipitating event(s), the waking event may be detected via the various physiological changes described above, or using any other suitable techniques. While the emphasis herein is on a wearable, continuous monitoring device, it will be understood that the device may also receive inputs from an external device such as a camera (for motion detection) or an infrared camera (for body temperature detection) that can be used to aid in accurately assessing various sleep states and transitions.

Thus the wearable, continuous physiological monitoring system may generally detect a waking event using one or more sensors including, for example, one or more of an accelerometer, a galvanic skin response sensor, a light sensor, and so forth. For example, in one aspect, the waking event may be detected using a combination of motion data and heart rate data.

As shown in step 612, the method 600 may include calculating a heart rate variability of the user at a moment in a last phase of sleep preceding the waking event based upon the heart rate data. While a waking event and a history of sleep states are helpful information for assessing recovery, the method 600 described herein specifically contemplates use of the heart rate variability in a last phase of sleep as a consistent foundation for calculating recovery scores for a device user. Thus, step 612 may also include detecting a slow wave sleep period immediately prior to the waking event, or otherwise determining the end of a slow wave or deep sleep episode immediately preceding the waking event.

It will be appreciated that the last phase of sleep preceding a natural waking event may be slow wave sleep. However, where a sleeper is awakened prematurely, this may instead include a last recorded episode of REM sleep or some other phase of sleep immediately preceding the waking event. This moment—the end of the last phase of sleep before waking—is the point at which heart rate variability data provides the most accurate and consistent indicator of physical recovery. Thus, with the appropriate point of time identified, the historical heart rate data (in whatever form) may be used with the techniques described above to calculate the corresponding heart rate variability. It will be further noted that the time period for this calculation may be selected with varying degrees of granularity depending on the ability to accurate detect the last phase of sleep and an end of the last phase of sleep. Thus for example, the time may be a predetermined amount of time before waking, or at the end of slow wave sleep, or some predetermined amount of time before the end of slow wave sleep is either detected or inferred. In another aspect, an average heart rate variability or similar metric may be determined for any number of discrete measurements within a window around the time of interest.

As shown in step 614, the method 600 may include calculating a duration of the sleep state. The quantity and quality of sleep may be highly relevant to physical recovery, and as such the duration of the sleep state may be used to calculate a recovery score.

As shown in step 618, the method 600 may include evaluating a quality of heart rate data using a data quality metric for a slow wave sleep period, e.g., the slow wave sleep period occurring most recently before the waking event. As noted above, the quality of heart rate measurements may vary over time for a variety of reasons. Thus the quality of heart rate data may be evaluated prior to selecting a particular moment or window of heart rate data for calculating heart rate variability, and the method 600 may include using this quality data to select suitable values for calculating a recovery score. For example, the method 600 may include calculating the heart rate variability for a window of predetermined duration within the slow wave sleep period having the highest quality of heart rate data according to the data quality metric.

As shown in step 620, the method 600 may include calculating a recovery score for the user based upon the heart rate variability from the last phase of sleep. The calculation may be based on other sources of data. For example, the calculation of recovery score may be based on the duration of sleep, the stages of sleep detected or information concerning the stages (e.g., amount of time in certain stages), information regarding the most recent slow wave sleep period or another sleep period/state, information from the GSR sensor or other sensor(s), and so on. The method 600 may further include calculating additional recovery scores after one or more other waking events of the user for comparison to the previously calculated recovery score. The actual calculation of a discovery score is described in substantial detail above, and this description is not repeated here except to note that the use of a heart rate variability measurement from the last phase of sleep provides an accurate and consistent basis for evaluating the physical recovery state of a user following a period of sleep.

As shown in step 630, the method 600 may include calculating a sleep score and communicating this score to a user.

In one aspect, the sleep score may be a measure of prior sleep performance. For example, a sleep performance score may quantify, on a scale of 0-100, the ratio of the hours of sleep during a particular resting period compared to the sleep needed. On this scale, if a user sleeps six hours and needed eight hours of sleep, then the sleep performance may be calculated as 75%. The sleep performance score may begin with one or more assumptions about needed sleep, based on, e.g., age, gender, health, fitness level, habits, genetics, and so forth and may be adapted to actual sleep patterns measured for an individual over time.

The sleep score may also or instead include a sleep need score or other objective metric that estimates an amount of sleep needed by the user of the device in a next sleep period. In general, the score may be any suitable quantitative representation including, e.g., a numerical value over some predetermined scale (e.g., 0-10, 1-100, or any other suitable scale) or a representation of a number of hours of sleep that should be targeted by the user. In another aspect, the sleep score may be calculated as the number of additional hours of sleep needed beyond a normal amount of sleep for the user.

The score may be calculated using any suitable inputs that capture, e.g., a current sleep deficit, a measure of strain or exercise intensity over some predetermined prior interval, an accounting for any naps or other resting, and so forth. A variety of factors may affect the actual sleep need, including physiological attributes such as age, gender, health, genetics and so forth, as well as daytime activities, stress, napping, sleep deficit or deprivation, and so forth. The sleep deficit may itself be based on prior sleep need and actual sleep performance (quality, duration, waking intervals, etc.) over some historical window. In one aspect, an objective scoring function for sleep need may have a model of the form:

$$SleepNeed = \text{Baseline} + f_1(\text{strain}) + f_2(\text{debt}) - \text{Naps}$$

In general, this calculation aims to estimate the ideal amount of sleep for best rest and recovery during a next sleep period. When accounting for time falling asleep, periods of brief wakefulness, and so forth, the actual time that should be dedicated to sleep may be somewhat higher, and this may be explicitly incorporated into the sleep need calculation, or left for a user to appropriately manage sleep habits.

In general, the baseline sleep may represent a standard amount of sleep needed by the user on a typical rest day (e.g., with no strenuous exercise or workout). As noted above, this may depend on a variety of factors, and may be estimated or measured for a particular individual in any suitable manner. The strain component, $f_1$(strain), may be assessed based on a previous day's physical intensity, and will typically increase the sleep need. Where intensity or strain is measured on an objective scale from 0 to 21, the strain calculation may take the following form, which yields an additional sleep time needed in minutes for a strain, i:

$$f(i) = \frac{1.7}{1 + e^{\frac{17-i}{3.5}}}$$

The sleep debt, $f_2$ (debt), may generally measure a carryover of needed sleep that was not attained in a previous day. This may be scaled, and may be capped at a maximum, according to individual sleep characteristics or general information about long term sleep deficit and recovery. Naps may also be accounted for directly by correcting the sleep need for any naps that have been taken, or by calculating a nap factor that is scaled or otherwise manipulated or calculated to more accurately track the actual effect of naps on prospective sleep need.

However calculated, the sleep need may be communicated to a user, such as by displaying a sleep need on a wrist-worn physiological monitoring device, or by sending an e-mail, text message or other alert to the user for display on any suitable device.

Figure 7:
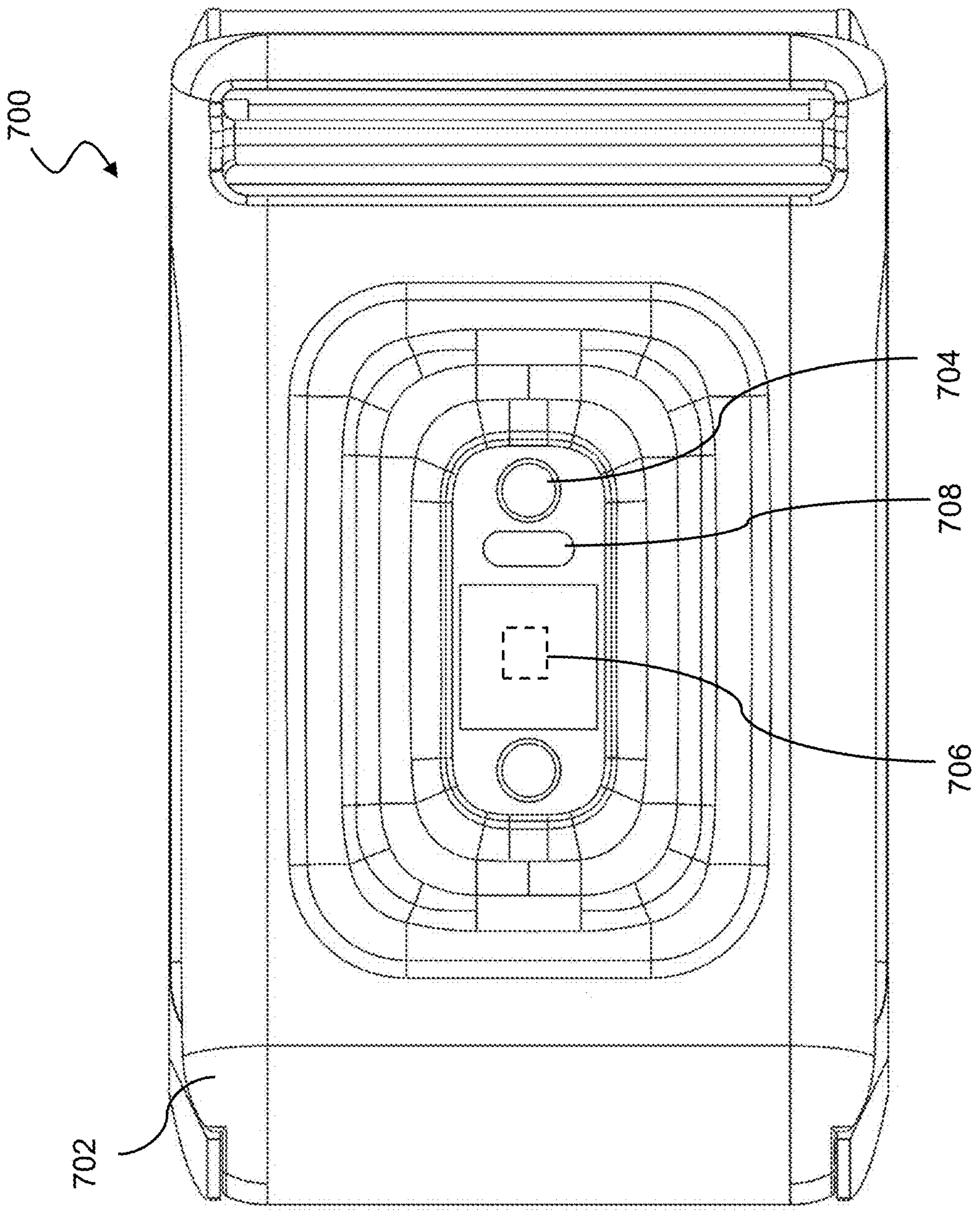
FIG. 7 is a bottom view of a wearable, continuous physiological monitoring device.

FIG. 7 is a bottom view of a wearable, continuous physiological monitoring device (the side facing a user's skin). As shown in the figure, the wearable, continuous physiological monitoring system 700 includes a wearable housing 702, one or more sensors 704, a processor 706, and a light source 708.

The wearable housing 702 may be configured such that a user can wear a continuous physiological monitoring device as part of the wearable, continuous physiological monitoring system 700. The wearable housing 702 may be configured for cooperation with a strap or the like, e.g., for engagement with an appendage of a user.

The one or more sensors 704 may be disposed in the wearable housing 702. In one aspect, the one or more sensors 704 include a light detector configured to provide data to the processor 706 for calculating a heart rate variability. The one or more sensors 704 may also or instead include an accelerometer configured to provide data to the processor 706 for detecting a sleep state or a waking event. In an implementation, the one or more sensors 704 measure a galvanic skin response of the user.

The processor 706 may be disposed in the wearable housing 702. The processor 706 may be configured to operate the one or more sensors 704 to detect a sleep state of a user wearing the wearable housing 702. The processor 706 may be further configured to monitor a heart rate of the user substantially continuously, and to record the heart rate as heart rate data without calculating a heart rate variability for the user. The processor 706 may also or instead be configured to detect a waking event at a transition from the sleep state of the user to an awake state, and to calculate the heart rate variability of the user at a moment in the last phase of sleep preceding the waking event based upon the heart rate data. The processor 706 may further be configured to calculate a recovery score for the user based upon the heart rate variability from the last phase of sleep.

The light source 708 may be coupled to the wearable housing 702 and controlled by the processor 706. The light source 708 may be directed toward the skin of a user's appendage. Light from the light source 708 may be detected by the one or more sensors 704.

Physiological signals acquired using the various different sensors described herein can be sensitive to conditions under which the physiological signal is obtained. Thus, for example, the physiological signal obtained during certain activities and/or under certain conditions can contain significant amounts of noise, or may have characteristics that vary according to the type of activity or other physical or physiological context. Accordingly, where it is desirable to continuously monitor a physiological signal, it can be advantageous to process the signal using the following techniques in order to reduce or eliminate the negative effects of confounding factors such as motion of the wearable, type of activity, the physical interface with a wearer's skin, weather or other ambient conditions, and so forth.

Figure 8:
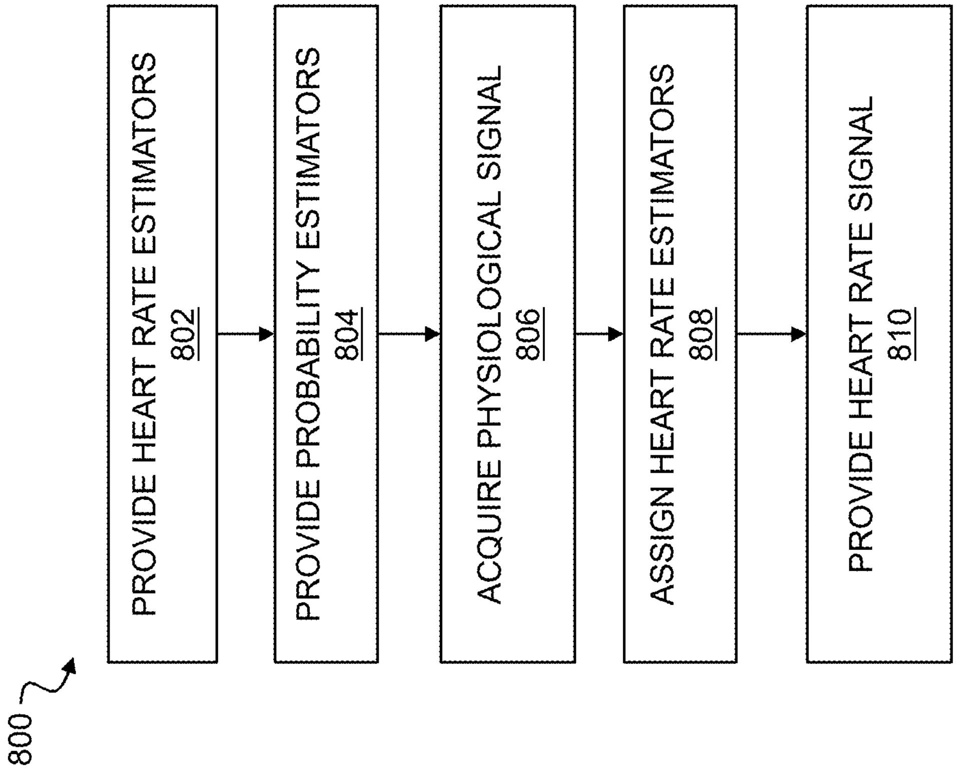
FIG. 8 is a flow chart illustrating a method for concurrent use of multiple physiological parameter estimation techniques.

FIG. 8 is a flow chart illustrating a method for concurrent use of multiple physiological parameter estimation techniques. For the sake of clarity of explanation, the method 800 is described with respect to heart rate estimation techniques. It should be appreciated, however, that the method 800 can be extended to the concurrent use of parameters estimation techniques for any of various different physiological parameters. As described in greater detail below, each estimation technique may be optimized for different activities and conditions to facilitate continuously and reliably estimating the physiological parameter.

The method 800 may be used in cooperation with any of the devices, systems, and methods described herein, such as by operating a wearable physiological monitoring device to perform one or more of the following steps. The wearable physiological monitoring device may, for example, be any of the devices described herein, and may include a processor, a memory, and a physiological sensor such as a photoplethysmography sensor or other heart rate or physiological monitoring system to obtain a physiological signal. The method 800 may also or instead be deployed using a server such as a remote server coupled in communication with a wearable physiological monitoring device and configured to receive data from the device and process the data using some or all of the steps below.

As shown in step 802, the method 800 may include providing a plurality of heart rate estimators for estimating a heart rate. Each one of the plurality of heart rate estimators may correspond to one of a number of predetermined measurement contexts for measuring the heart rate with a wearable physiological monitor. For example, each one of the plurality of heart rate estimators may be optimized to one of a number of predetermined measurement contexts so that the estimator is optimized to provide an accurate calculation of the heart rate in the corresponding context. In general, the predetermined measurement contexts may relate to motion, ambient conditions, and combinations thereof. For example, it may be useful to process data using one technique or algorithm when outdoors, e.g., in the presence of bright sunlight or darkness of night, while a different technique may be more useful while on a treadmill in an indoor facility with fixed, moderately bright lighting. Thus, the number of predetermined measurement contexts may include one or more of an indoor activity, an outdoor activity. Similarly, weather conditions such as rain or temperature may affect the physical interface to a body, and conditions such as cloudiness or rain may impact measurements by altering ambient lighting conditions. Thus, the number of predetermined measurement contexts may also or instead include an ambient weather condition.

In general, the heart rate signal estimated by the plurality of heart rate estimators may be a time domain heart rate signal such as a photoplethysmography signal or other time domain measure of cardiac activity. In another aspect, the estimators may be used to directly estimate other derivative signals of interest such as heart rate variability or the like. Thus the heart rate signal may be a heart rate variability signal, peak-to-peak interval signal or other signal that would otherwise be calculated from the time domain heart rate.

Additionally, or alternatively, the number of predetermined measurement contexts may include one or more of active, sedentary, and sleeping, any of which may affect skin surface conditions, motion, and other factors influencing the selection of an estimator for heart rate or any other physiological signal. The number of predetermined measurement contexts may also or instead include one or more types of physical exercise. For example, different estimators may provide better results for activities that vary significantly in terms of physical motion, strain, and so forth, particularly in activities such as bicycling, swimming, and jogging where the rate of movement and range of motion for the physiological monitoring device is likely to vary widely. Similarly, other activities such as basketball or tennis may be less prone to recurring periodic motions, and may be amenable to treatment with other, different estimators of heart rate. Thus in another aspect, the number of predetermined measurement contexts may include one or more types of motion of the wearable physiological monitor based on motion data from one or more motion sensors in the wearable physiological monitor. In another aspect, different estimators may be more accurate for different absolute heart rates (e.g., high heart rates or low heart rates) or may be more accurate for different relative heart rates (e.g., a percentage of the resting heart rate or maximum heart rate). Accordingly, in certain embodiments, the number of predetermined measurement contexts may include a current heart rate estimated for the wearable physiological monitor, which may, as noted above, include a relative heart rate or an absolute heart rate.

The heart rate estimators may include a frequency domain peak detector. For example, the heart rate estimators may include a fundamental frequency of the physiological signal in the frequency domain or a harmonic product spectrum for the physiological signal. Additionally, or alternatively, the heart rate estimators may include a fundamental frequency of a complex cepstrum for the physiological signal. The heart rate estimators may also or instead include a peak detector for one or more harmonics of the fundamental frequency.

In certain implementations, heart rate estimators may include at least one estimator with a high-Q time domain filter for the physiological signal around a predetermined frequency of interest. As an example, the heart rate may be estimated, and the beats can be identified in the time domain with this signal. The identification of the beats can be based on a likelihood analysis. A higher likelihood can be ascribed, for example, to higher rhythmicity of the signal. The absence of alternans (beat-to-beat variation in amplitude) may be additionally, or alternatively, associated with a higher likelihood. As another nonexclusive example, a higher likelihood can be associated with not finding a regular set of beats at ½ the estimated heart rate.

Further, or instead, the heart rate estimators may include an estimator that tracks peaks in the physiological signal relative to a motion signal. For example, the actual peaks in the physiological signal can be tracked over time and a motion signal frequency (e.g., based on a signal from a motion sensor) can be similarly tracked. Continuing with this example, when the actual peaks in the physiological signal and the motion signal frequency converge at the same estimated value, the likelihood that this peak accurately represents the physiological parameter may be increased. Similarly, when the actual peaks in the physiological signal and the motion signal frequency diverge, the likelihood may decrease or return to normal.

The heart rate estimator may also or instead use any physiological signal or data available to the monitoring device, or available in a post processing context, such as body temperature, breathing rate, and so forth. More generally, the heart rate estimators may be any estimators that usefully facilitate a calculation of a heart rate under one or more conditions of interest. It will be appreciated that while the discussion herein emphasizes the use of heart rate signals in particular, the techniques disclosed herein may also or instead be used on any other physiological signal of interest. Thus, rather than a heart rate estimator, the estimators may include estimators of any time-based physiological signal of interest, with suitable adaptations to the monitoring system and the remaining method steps as would be appreciated to one of ordinary skill in the art, and all such adaptations and modifications are intended to fall within the scope of this disclosure.

As shown in step 804, the method 800 may include providing a plurality of probability estimators. Each one of the plurality of probability estimators may correspond to one of the plurality of heart rate estimators, with each one of the plurality of probability estimators providing a likelihood that the corresponding heart rate estimator is accurately estimating the heart rate based on a physiological signal from the wearable physiological monitor.

The probability estimators may in general provide a manner for calculating relative likelihoods that each of the plurality of heart rate estimators (or other physiological signal estimators) is producing an accurate or otherwise reliable result. This may be independently calculated for each estimator using any suitable scoring system or merit function, or this may be expressed as relative values where the sum of the likelihoods for all of the estimators is 1.0 or 100 percent, or some other normalized value. In one aspect, the probability estimators may use time-based information, e.g., where the most recently selected estimator, or one of the last several recently selected estimators (e.g., last two, three, five, or some other number) receives an increased score based on an inference that the estimator remains accurate or relevant. Thus, for example, where an indoor estimator has been selected, that estimator may continue to be applied until a strong contrary inference is presented for an outdoor estimator.

The probability estimators may also be varied or weighted in different ways. For example, the probability estimators may be hierarchically arranged so that groups of estimators are scored in groups independently from one another, relative to one another, or some combination of these. In another aspect, probability estimators may be weighted or adjusted based on other data external to the current physiological monitoring such as GPS data, user history data, weather information, and so forth.

In one aspect, suitably likelihood functions may be analytically derived from known characteristics of the physiological system, physical activities, monitoring device, and so forth. In another aspect, suitable likelihood functions for use as probability estimators may be derived using representative data sets and ensemble classifiers, as described for example in U.S. Prov. App. No. 62/218,017 filed on Sep. 14, 2015 and incorporated by reference herein in its entirety. More generally, any techniques useful for discriminating among multiple options for calculating a heart rate or other time-based metric of interest from physiological data may be usefully employed as a probability estimator as contemplated herein.

As shown in step 806, the method 800 may include acquiring a physiological signal from the wearable physiological monitor over an interval. The interval may be any time interval of interest subject to the data recording and storage limits of the monitoring system (including any remote processing and storage resources), and may be made up of segments (e.g., discrete segments), which may, for example, be mutually exclusive segments that together cover the entire interval or a predetermined portion thereof. In another aspect, the segments may be overlapping segments or any other windowed or otherwise selected and arranged segments useful for applying probability estimators as contemplated herein. The physiological signal may, for example, include a photoplethysmography signal as described above, or any other physiological signal indicative of a physiological state that might vary over time such as a breathing rate, body temperature, pulse oxygen level, and so forth.

As shown in step 808, the method 800 may include, for each segment of the interval, assigning one or more selected ones of the plurality of heart rate estimators to the segment according to the likelihood of accurately estimating the heart rate in the segment. In one aspect, the heart rate estimator with the highest score or likelihood may be selected to calculate the heart rate for that interval. In another aspect, additional rules or the like may be applied to select among various candidates. Thus for example, assigning one of the heart rate estimators to a segment may include favorably weighting one or more immediately prior estimators prior to selecting one of the heart rate estimators for assignment to the segment. In a post-processing context, this may also or instead include favorably weighting one or more subsequent heart rate estimators. Further, whether or not these temporally adjacent heart rate estimators are weighted more favorably may depend on a relative score or confidence associated with them, so that a very highly scored and immediately adjacent estimator is more likely to be applied to a current segment. In another aspect, estimators may be hierarchically arranged to control the assignment process. For example, where one heart rate estimator is selected, other heart rate estimators may be more favorably weighted or less favorably weighted relative to other estimators according to the nature of the relationship among estimators within the group—e.g., based on whether selection of one estimator in the group makes other estimators in the group more or less likely to occur in temporally adjacent segments.

In another aspect, a threshold or the like may be applied to discern circumstances in which none of a set of heart rate estimators appears to be providing reliable data. In this case, any number of techniques may be used to interpolate heart rate data until a reliable signal is restored. For example, this may include using an immediately prior estimator, using a simple fundament frequency, using an average of the physiological signal over some preceding interval, or any other suitable technique. Alternatively, the error condition may be reported as missing data and processing may be suspended or terminated until a reliable physiological signal is reacquired.

It will be understood that a variety of alternative implementations of this general approach may usefully be employed. For example, a preliminary estimate may be created of a most probable heart rate based on one or more factors such as a prior heart rate, a subsequent heart rate, or a history for a user of the wearable physiological monitor, as well as combinations of the foregoing and/or any other suitable information or inputs. This preliminary estimate may also or instead be filtered to remove motion artifacts as described herein. In any case, after creating a preliminary estimate, this preliminary estimate may be adjusted by applying the plurality of heart rate estimators according to the probability estimators to increase a probability of an accurate estimate as generally contemplated herein.

In another aspect, multiple heart rate estimators may be combined for concurrent use in order to increase accuracy. Similar to a traditional multiple imputations approach, the fusion step in such a selection-fusion algorithm may combine the results of the individual classifiers to boost-up the overall classification accuracy. In multiple imputations, the results are combined in a simple fashion:

$$\Gamma_{MI}(x) = \frac{1}{q}\sum_{i=1}^{q}\Gamma(x; I_i)$$

where $I_i$ is the ith imputation of the incomplete data and q represents the number of imputations. The number of required imputations is estimated by the Rubin's imputation efficiency law quantified by $$\text{efficiency} = \frac{1}{\left(1 + \frac{\gamma}{q}\right)^{0.5}}$$

where $\gamma$ is the fraction of the missing values in the data. The efficiency is a value between 0 and 1 and shows the performance of q imputations compared with the infinite number of imputations. When q is small compared with $\gamma$, increasing q improves the efficiency. However, when q is large enough, its further increments do not improve the efficiency considerably. This criterion may be used to select appropriate number of imputations.

In the contemplated selection-fusion method, the distribution of the missing values in the feature space may be used to improve the performance. In contrast to a multiple imputation approach where all imputations have the same weight, in the proposed approach, the classification accuracy of each classifier for a given testing sample can be used to weigh the outputs. Since a subset of samples and features, not the whole data, is involved in the training of each classifier, a specific subset may be advantageous depending on the sample being tested. Thus, in the fusion step, the aggregation step may be the weighted combination:

$$\Gamma_{BB}(x) = \frac{1}{\sum_i 1/\varphi_{i,x}} \sum_{i=1}^{n(B)} \frac{1}{\varphi_{i,x}} \Gamma(x; S_{\theta_i})$$

where $\varphi_{i,x}$ is the relative inaccuracy or expected error of $\Gamma(x; S_{\theta i})$ estimated at x which depends on the accuracy of $\Gamma(x;S_{\theta i})$ around x and the number of features used in the classifier.

By way of non-limiting example, two factors may be usefully considered in determining a classifier's expected error qix for a specific sample: (1) general accuracy of the classifier and (2) similarity between the features of the samples in the training set and those of the testing sample. Thus, the local accuracy of the classifier should be calculated for each individual testing sample based on two factors: (1) the number of samples in the training set that are in the neighborhood of the testing sample and (2) the similarity between the subset features ($\theta_i$) and the existing features for the testing sample.

Next a similarity may be estimated between the training and testing samples. If all features are identically informative, the similarity between the missing value patterns in a subset and the testing sample can be characterized by $$\hat{\theta}_{x_i}^T \theta_i$$

where $\hat{\theta}_{x_i}$ and $\theta_i$ are the feature sets available for the testing sample $x_j$ and the ith subset, respectively. To take the relative quality of the features into account, the similarity is written as $$\theta_{x_i}^T K \theta_i$$

where K is a diagonal matrix to weigh the features based on their information level.

A value for $\varphi_{i,x}$ may be calculated using $$\varphi_{i,x} = \left(\Gamma(x; S_{\theta_i}) - Y(x)\right)^2 f\left(\theta_{x_i}^T K \theta_i\right)$$

where Y(x) is the label of x. When there is no ranking of the features, K is equal to the identity matrix. Here, $f$ is a non-increasing function that calculates the effect of similarity between the feature spaces of the classifier and the testing sample. For simplicity, we define $f(u)$ as 1/u. When there are no common features, $f$ removes the effect of the classifier from aggregation. Alternatively, when all features are present, $f$ does not change the error measure.

The preceding equation can be calculated for the training data. However, for a testing sample, it needs to be estimated since Y(x) is unknown. To estimate $\varphi_{i,x}$ easily, all of the training samples in the vicinity of the testing sample may be used:

$$\hat{\varphi}_{i,x'} = \frac{1}{\eta_{x'}} \sum_{x \in Training} dis(x, x')\varphi_{i,x}$$

where $$(dis(x, x'))^2 = \|x - x'\|^2 f\left(\theta_x^T K \theta_{x'}\right)$$

and $$\eta_{x'} = \sum_{x \in Training} dis(x, x')$$

It will be noted that the distance between the two samples is modulated by their common features through the second term. Using this fusion technique, a number of heartbeat estimators may be used in combination to improve accuracy of an estimated physiological signal such as a heart rate. Thus in one aspect, assigning one or more selected ones of the plurality of heart rate estimators to a segment of a measurement interval may include fusing multiple heart rate estimators for the segment using the techniques described above and using this fused estimator to determine a heart rate for the segment, e.g., by estimating the heart rate signal with a fused estimator or applying the fused function to adjust a heart rate determined using another estimator or technique.

As shown in step 810, the method 800 may include providing a heart rate signal over the interval based upon the physiological signal and the selected ones of the plurality of heart rate estimators. In general, the heart rate estimator assigned to each segment may be used to calculate the heart rate for that segment. With a heart rate signal calculated from raw source data (e.g., the sensor data captured directly by the monitoring device) for each segment using an accurate estimator in this manner, the heart rate signal for the entire interval can be determined as a combination of the heart rate signal for each of the individual segments.

It should be appreciated that, because the heart rate signal provided in step 810 is continuous, the method 800 may further include using the heart rate signal for assessment of health, fitness, recovery, and/or sleep according to any one or more of the various different methods described herein that rely upon or benefit from a continuous physiological signal. For example, the method 800 may further include determining heart rate variability over the interval based upon the heart rate signal. The heart rate variability can be determined according to any or more of the various different methods described herein, such as the methods described above with respect to FIG. 3.

This approach provides significant advantages over other techniques present in the art. The use of multiple estimators and corresponding likelihood functions presents additional processing and storage requirements generally unsuited to a wearable device. Further there would appear to be little motivation to adapt existing wearable monitors for this use where the primary purpose is display of a current heart rate or acquisition of periodic heart rate measurements over time. However, where a metric such as workout intensity is being calculated, the result is highly dependent on heart rate variability throughout the exercise activity, and missing data may lead to substantial errors in the appraisal of a workout's difficulty, or similarly, the recovery obtained from a period of rest or sleep. By facilitating the derivation of a more accurate continuous measurement of heart rate variability, downstream calculations of metrics that are highly sensitive to accurate HRV measurements—such as exercise intensity and recovery—can be substantially improved.

According to the foregoing, a system contemplated herein includes a memory and a server. The memory may generally be configured to store data corresponding to a physiological signal over an interval, the physiological signal acquired by a wearable physiological monitor. The server may be configured to assign, for each segment of the interval, one or more selected heart rate estimators of a plurality of heart rate estimators based on a likelihood of accurately estimating the heart rate in the segment and to provide a continuous heart rate signal over the interval based upon the physiological signal and the one or more selected heart rate estimators, each heart rate estimator of the plurality of heart rate estimators optimized for one of a number of predetermined measurement contexts for measuring the heart rate with the wearable physiological monitor.

In the system, the likelihood of accurately estimating the heart rate in the segment may be based on a plurality of probability estimators, each one of the plurality of probability estimators corresponding to one of the plurality of heart rate estimators, and each one of the plurality of probability estimators providing a likelihood that the corresponding heart rate estimator is accurately estimating the heart rate based on the physiological signal from the wearable physiological monitor. In another aspect, the plurality of heart rate estimators may include at least one or more of a frequency domain peak detector, a fundamental frequency of a harmonic product spectrum for the physiological signal, a fundamental frequency of a complex cepstrum for the physiological signal, a high-Q time domain filter for the physiological signal around a predetermined frequency of interest, and an estimator that tracks peaks in the physiological signal relative to a motion signal.

Figure 9:
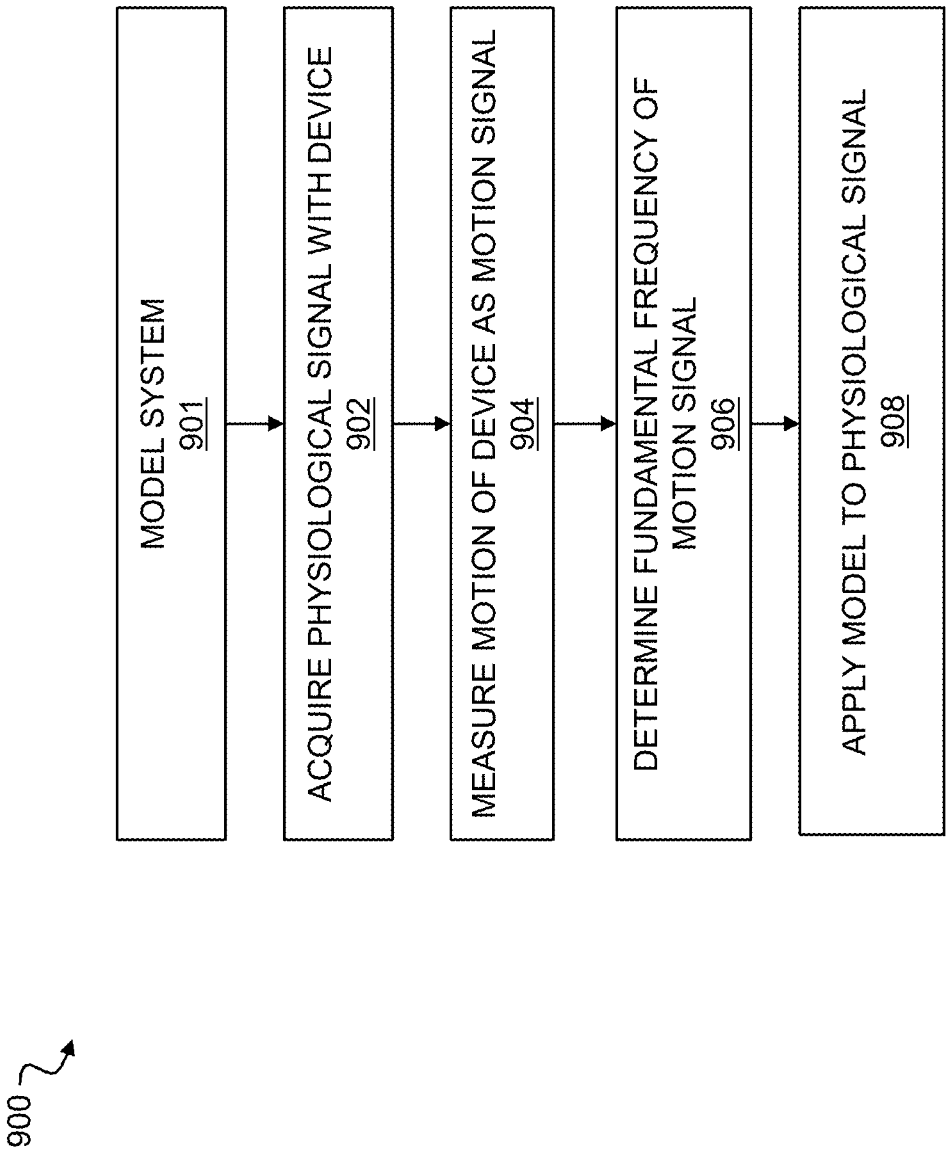
FIG. 9 is a flow chart illustrating a signal processing algorithm for removing motion artifacts from a physiological signal.

FIG. 9 is a flow chart illustrating a signal processing algorithm for removing motion artifacts from a physiological signal. Removing motion artifacts from the physiological signal according to method 900 can reduce the likelihood that movement of a wearer of a wearable continuous physiological monitoring device will interfere with continuous and reliable physiological monitoring. That is, in general, the method 900 can facilitate physiological monitoring in a manner that is robust with respect to motion typically associated with exercise.

The method 900 may be used in cooperation with any of the devices, systems, and methods described herein, such as by operating a wearable physiological monitoring device to perform one or more of the following steps. The wearable physiological monitoring device may, for example, include a processor, a memory, and a physiological sensor (e.g., one or more light emitting diodes and one or more light detectors arranged to obtain heart rate data from a wearer of the wearable device) to obtain a physiological signal. Additionally, or alternatively, the method 900 may be implemented on a server (e.g., a remote server) in communication with a wearable physiological monitoring device to perform one or more of the following steps. As an example, the server can receive a physiological signal obtained by the wearable physiological monitoring device and one or more steps of method 900 may be performed at the server.

As shown in step 901, the method 900 may include modeling a system that includes a wearable physiological device and a user. In general, the modeling may seek to determine a relationship between motion by the wearable device and physiological measurements taken by the device, e.g., optical signals from a photoplethysmography system, and may result in a model suitable for reducing or eliminating motion artifacts from a physiological measurement. The relationship may be determined using any suitable modeling techniques including, without limitation, regression analysis, physical modeling, empirical modeling, matched filtering, machine learning, or any other suitable time domain, frequency domain, probabilistic, or other techniques. In one aspect, a weighting function may be derived with minimum weights at dominant peaks of an accelerometer spectrum, e.g., for each of three accelerometer signals in a three-dimensional motion sensing system. The dominant peaks may also or instead be estimated and separately applied to form a weighting function for motion cancellation. In another aspect, various harmonics may also or instead be used to form a weighting function to account for modulation of three-dimensional motion within the physical system. In another aspect, motion projection can be employed to derive a model for projecting the motion signal into a common space with the optical signal (or other sensor signal) for direct mathematical combination. A model that relates the motion of the device to a physiological measurement may also or instead be based on a multiplicative modulation of the physiological signal and the motion signal. With this model, a set of harmonics of the underlying physiological signal and the motion will be observed. The model, in certain instances, may be a function of the motion normal to the tissue.

Suitable techniques for developing a model for a relationship between physical motion of a wearable monitor and a physiological signal obtained from a sensor of the wearable monitor are described by way of non-limiting examples in U.S. Prov. App. No. 62/218,017 filed on Sep. 14, 2015 and incorporated by reference herein in its entirety. These any other techniques may usefully be employed to derive a model suitable for use in the method 900 contemplated herein.

As shown in step 902, the method 900 may include acquiring a physiological signal with the device over time. The physiological signal may be indicative of a physical state of a wearer of the device. In one aspect, the physiological signal may be a signal indicative of a heart rate of the wearer. By way of example, and not limitation, such a physiological signal may be acquired with a photoplethysmography (PPG) detector in the device. The PPG detector, it should be appreciated, may be any of the various different PPG detectors described herein. The physiological signal may also or instead include any optical, electrical, acoustic, or other signal indicative of a physical state of the user, such as a heart rate, heart rate variability, body temperature, breathing rate, breathing volume, pulse oxygen, blood pressure, and so forth.

As shown in step 904, the method 900 may include measuring motion of the device as a motion signal over time. As an example, the device may include one or more accelerometers, and the measured motion of the device may be based on a motion signal from the one or more accelerometers over time. It should be appreciated that the one or more accelerometers may be any of the various, different accelerometers generally known in the art and, therefore, may include multi-axis accelerometers. For example, the device may include a three-axis motion sensing system that includes three accelerometers to capture motion data in three-dimensions, e.g. along three orthogonal axes. In addition, or in the alternative, measuring motion of the device may include detecting motion in a predetermined axis (e.g., an x-, y-, or z-axis) of the device, which may be aligned with a single accelerometer axis or derived from a multi-axis sensing system.

As shown in step 906, the method 900 may include determining a fundamental frequency of a spectrum of the motion signal. This may include determining the fundamental frequency using any suitable technique or combination of techniques. For example, a dominant peak in the spectrum of the motion signal may be identified. Further, or instead, determining the fundamental frequency may include identifying the fundamental frequency using at least one of a harmonic product spectrum and a complex cepstrum of the spectrum of the motion signal. A variety of useful models as contemplated in step 901 may conveniently characterize motion artifacts as a set of harmonics of a fundamental motion frequency. Thus a model to address these artifacts may usefully modify a sensor signal using a group of notch filters that selectively attenuate the physiological signal (in a weighted or unweighted manner, or some combination of these) at the fundamental frequency of the motion signal and any number of harmonics thereof. As a significant advantage, this approach facilitates artifact mitigation using a measurement of a single fundamental frequency of the motion signal (or alternatively, three fundamental frequencies along three orthogonal axes). In certain implementations, the spectrum of the motion signal may be preprocessed to remove one or more artifacts arising from time domain discontinuities in the motion signal. An exemplary preprocessing step may include discarding any peaks caused by a 1/f frequency distribution, such as might be caused by discontinuities in the motion signal.

As shown in step 908, the method 900 may include applying a model to the physiological signal to mitigate motion artifacts. In one aspect, this may include a notch filter to the physiological signal, such as a notch filter or group of notch filters that attenuate a fundamental frequency of the motion signal and one or more related frequencies of the motion signal such as harmonics of the fundamental frequency. The filter or group of filters may thus provide a filtered physiological signal with reduced motion artifacts for subsequent processing.

According to one aspect of the invention, physiological data acquired or estimated using the techniques described herein may be improved by concurrently assessing data quality based on data-driven machine learning or other suitable techniques using statistical analysis, pattern matching, artificial intelligence, and so forth. These techniques may be used instead of, or in addition to, the other heart rate calculations described herein in order to determine whether and how to use physiological data based on a quality metric such as a likelihood that the current data is accurate. By deriving a quality estimation engine from large data sets, such as one containing thousands of hours of recorded data for thousands of activities and workouts by many users, accurate estimates of quality may be obtained that are indicative, e.g., of the confidence that an estimated heart rate is within a certain range of beats-per-minute from the true heart rate, or that otherwise provide a suitable measure of quality, accuracy, or the like.

Figure 10:
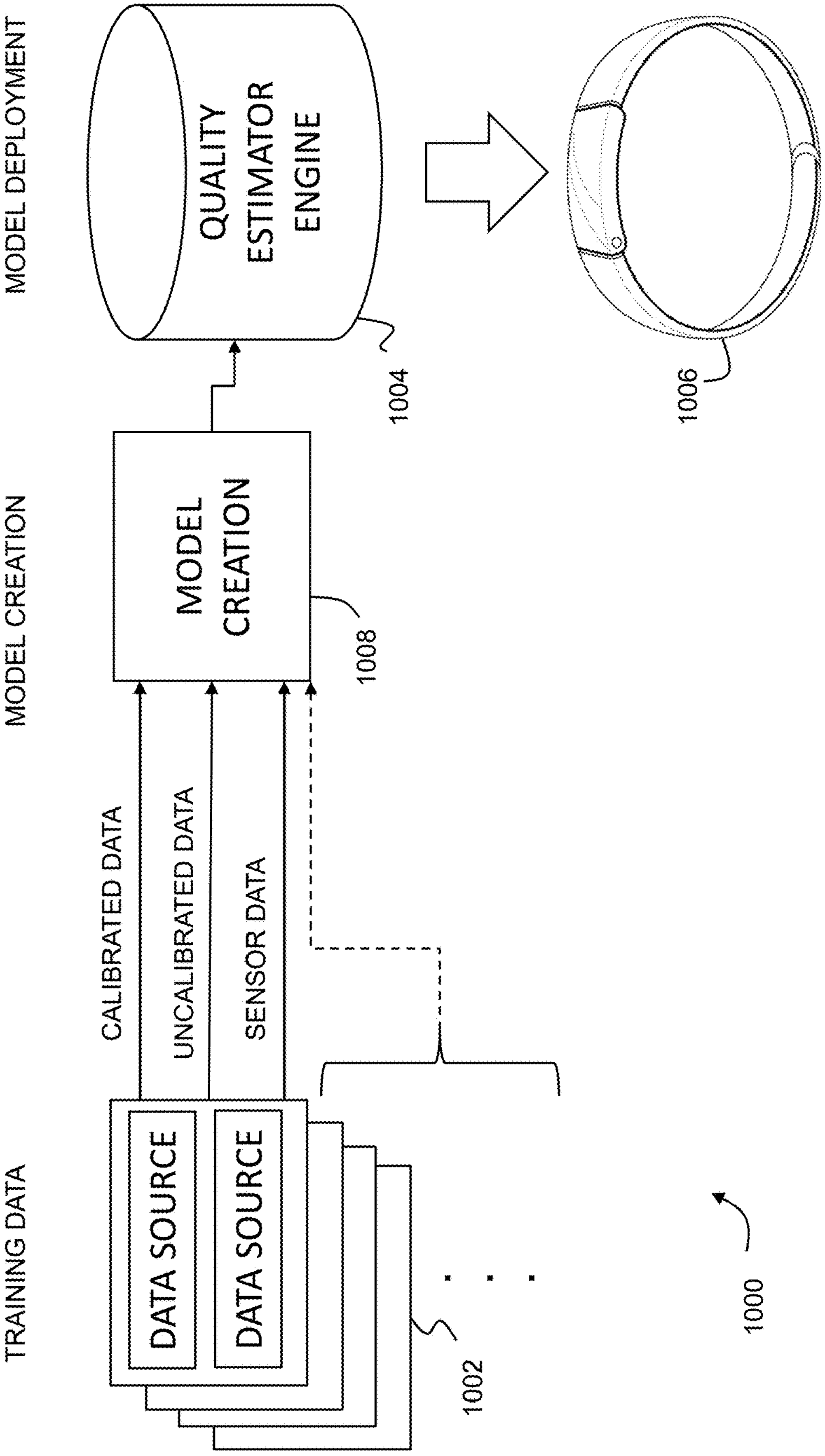
FIG. 10 shows a system for evaluating physiological data accuracy.

FIG. 10 shows a system for evaluating physiological data accuracy. In the system 1000, a number of subjects 1002 may be used to acquire suitable data and create a model that can be deployed on a wearable device 1006 such as any of the wearable devices described herein.

In general, each subject 1002 may be a user with a number of data sources such as wearable physiological monitors or other sensors or the like. In a data acquisition phase, training data may be acquired while each subject 1002 engages in various activities over time. This may include activities such as sleeping, resting, exercising, or any of the other categories or sub-categories of activities described herein. During these activities, each subject 1002 may provide calibrated data from a data source that is presumed to provide accurate data. For example, a data source such as a chest strap or electrocardiography (EKG) device may be assumed to provide accurate heart rate data, and may be used as a ground truth source of calibrated data for modeling heart rate accuracy. More generally, any other physiological data may usefully be obtained from a calibrated source that can reasonably be assumed to provide an accurate measurement of a corresponding physiological signal such as, without limitation, brain activity, pulse oxygen, blood pressure, and so forth.

Each subject 1002 may also provide uncalibrated data. For example, a data source such as a wearable physiological monitoring device may be used to acquire a physiological signal concurrently with the calibrated data. In general, this source of uncalibrated data will represent the same (or a similar) physiological measurement as the calibrated data, but from a source of unknown, variable, or unreliable accuracy. Thus, for example, where the calibrated data includes heart rate data from a chest strap or EKG, the uncalibrated data may be photoplethysmography data from a wrist-worn wearable device or the like.

Each subject 1002 may also provide sensor data. This may include data from the same data source that provides the uncalibrated data, or from other sensors on the uncalibrated data source. For example, photoplethysmography uses light intensity measurements to derive heart rate data. These light intensity measurements may also be used to characterize a more general data acquisition context, e.g., by varying over time in response to user movements, activity levels, and so forth. In one aspect, sensor data may include time domain features of the measurement signal such as a maximum value, minimum value, range, frequency (in any suitable bins), and so forth. This may also include descriptive statistics for the time domain signal such as a median, average, variance, and so forth. The sensor data may also or instead include frequency domain features such as the magnitude and frequency of any number of peaks, harmonics, and so forth. For example, this may include the first, second, and third largest peaks in the frequency domain data for the optical sensor(s) and/or the corresponding peak values, which may usefully be measured before and after low pass filtering. This may also include data based on the derived heart rate data, such as the last heart rate estimate obtained from the optical signal, the closest frequency domain peak to the last heart rate estimate, and so forth. In another aspect, other data such as accelerometer data may usefully be employed. For example, this may include the mean, range, minimum, and maximum of accelerometer data on each of the X, Y and Z axes for the accelerometer. This may also or instead include the first, second, and third largest peaks in the frequency domain data for the accelerometer data and/or the corresponding peak values, which may be measured independently in the X, Y and Z directions, or as a single, combined vector magnitude for these three axes. As with the optical data, this frequency domain information may usefully be evaluated before and after low pass filtering. The sensor data may usefully be windowed in any suitable range for processing as contemplated herein. For example, a ten second window has been demonstrated to usefully balance processing requirements and the usefulness and accuracy of the resulting model. However, smaller or larger windows may also or instead be employed, and overlapping windows may also or instead be used to more finely localize the data acquisition context for use in creating a quality estimator engine.

A model creation system 1008 may process the calibrated data, uncalibrated data, and sensor data to generate a quality estimator engine that can provide a quality metric for the uncalibrated data based on the sensor data. For example, the quality metric may provide a probability that the uncalibrated data is accurate, or within a predetermined threshold of the calibrated data. This may include computer code or the like executing on a computer to create the quality estimator engine.

The model creation system 1008 may, for example, include applying artificial intelligence or machine learning techniques to train a model to evaluate accuracy, e.g., the likelihood of being within a predetermined threshold, based on a current data acquisition context for the uncalibrated data source based on the sensor data. In one aspect, for each measurement sample or window, the calibrated data may be compared to the uncalibrated data to determine whether the uncalibrated data is sufficiently close to the calibrated data to be considered accurate. By way of non-limiting example, the uncalibrated data and calibrated data may represent a heart rate, and the predetermined threshold for accuracy may be four beats per minute. In this example, if the calibrated data indicates eighty beats per minute and the uncalibrated data indicates eighty-two beats per minute, then the uncalibrated data is within the threshold and the uncalibrated data may be considered accurate. By contrast, in this example, if the uncalibrated data indicates eighty-five beats for minute, then this exceeds the threshold and the data is considered inaccurate. In order to capture this evaluation for training purposes, uncalibrated data within the threshold may be assigned a one, and uncalibrated data outside the threshold may be assigned a zero. A machine learning algorithm may then be trained to identify accurate versus inaccurate data based on the corresponding sensor data (which may optionally include or exclude the physiological measurement of interest, e.g., the heart rate). While a binary system (e.g., a '1' for accurate and '0' for inaccurate) may usefully be applied to provide training data for the quality estimator engine, other measures may also or instead be used. For example, a variable probability may be applied where, for example, the current sensor data yields an uncalibrated result that is 90% likely to be accurate, either for a point measurement, for a window, for a range of heart rates, or some combination of these.

It will also be appreciated that a range of techniques may usefully be employed to relate the sensor data to an estimate of data quality such as a likelihood of accuracy. For example, decision trees can usefully be employed to divide the feature space for sensor data into regions with various likelihoods of accuracy, and a machine learning random forest may also or instead be employed, e.g., to mitigate overfitting of data. Other techniques may also or instead be employed including without limitation machine learning techniques such as neural networks, deep learning, support vector machines, nearest neighbor algorithms, Bayesian networks, and so forth. Predictive modeling techniques may also or instead be used, such as linear regression, multinomial logistic regression, and so forth. While large decision trees and random forests can, in particular, require substantial processing resources to create, they also can provide several advantages. For example, decision trees can yield compact, computationally efficient models for the quality estimate engine that generally scale linearly in size and execution speed with the feature space. This can usefully permit the resulting engine 1004 to be ported to a wearable device 1006 in a manner consistent with the processing requirements and memory capacity of a typical embedded system.

When the quality estimator engine 1004 has been generated with the model creation system 1008 based on the data from the subjects 1002, the engine 1004 may be ported to a wearable device 1006 and stored in memory for use during acquisition of new physiological data. The quality estimator engine 1004 may then be used by the wearable device 1006 to calculate a probability that a measurement of the physiological data is accurate based on corresponding feature data, or otherwise provide a data quality metric as contemplated herein.

The wearable device 1006 may be any of the wearable devices described herein. In general, the wearable device 1006 may include a wrist strap or other component for securing the wearable device 1006 to a user's body. The wearable device 1006 may also include one or more sensors for capturing physiological data characterizing a physiological measurement for a user of the wearable device and feature data characterizing a timewise data acquisition context for the physiological data. This may include any of the sensors described herein, and as noted above, the sensors for the physiological data may be the same sensors used to capture the feature data, or different sensors, or some combination of these. The wearable device 1006 may also include a memory storing the quality estimator engine 1004, as well as a processor configured by computer executable code to evaluate the accuracy of uncalibrated data from the sensors. For example, the processor may be configured to perform the steps of receiving physiological data and feature data from the one or more sensors, calculating a probability that the physiological data is accurate for a window of measurements by applying the quality estimator engine to a distribution of values for the physiological data and corresponding values for the feature data, and storing the probability as a measure of quality for the physiological data within the window. This quality metric may be used for further processing on the wearable device 1006, and may also be reported with other physiological data to a remote processing resource for storage and additional processing.

Figure 11:
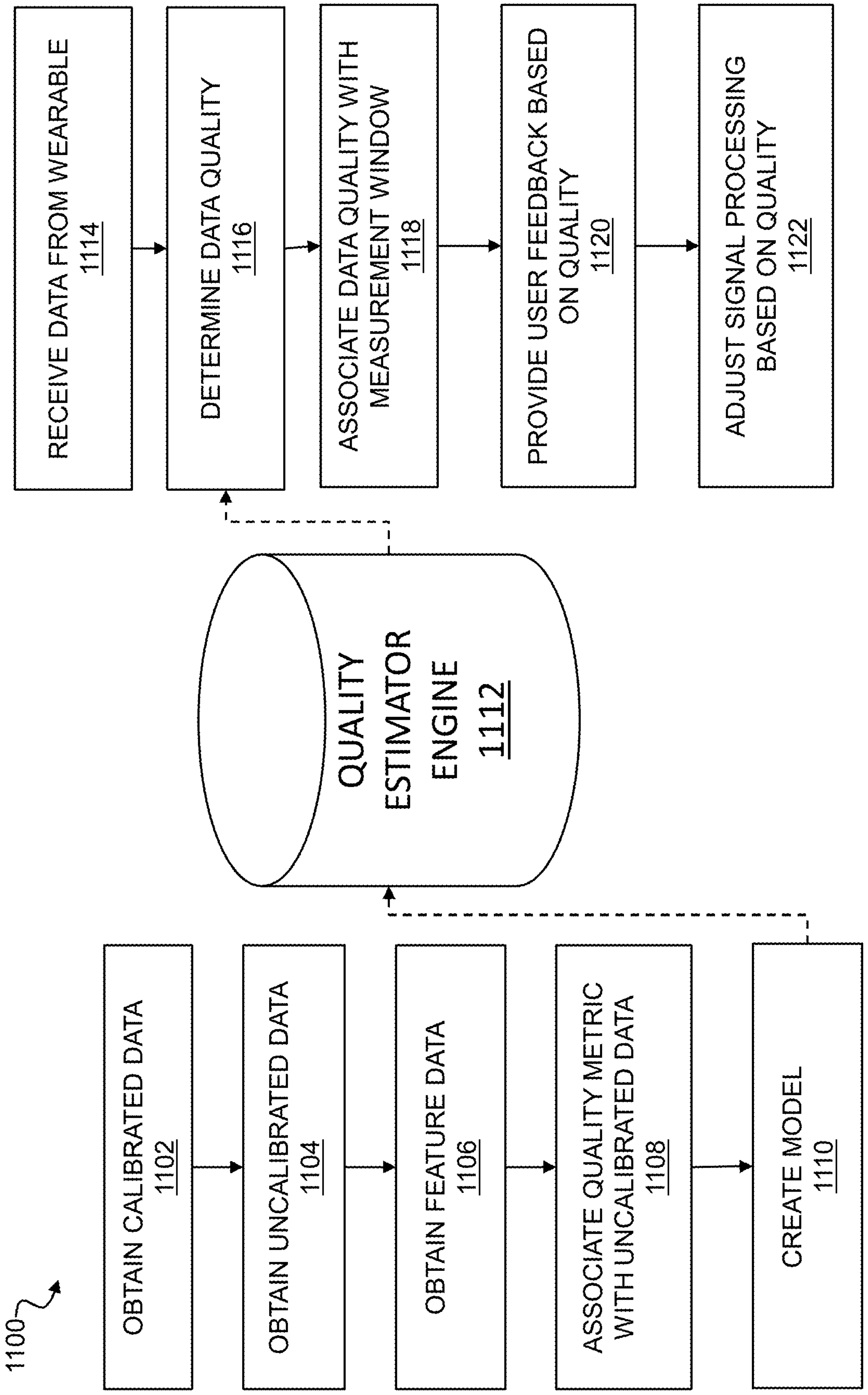
FIG. 11 is a flow chart illustrating a method for evaluating the accuracy of physiological data from an uncalibrated data source.

FIG. 11 is a flow chart illustrating a method for evaluating the accuracy of physiological data from an uncalibrated data source. In general, the method 1100 includes acquiring uncalibrated data, calibrated data, and feature data from a number of subjects, and then processing this training data to obtain a model for evaluating the accuracy of the uncalibrated data based on the feature data. This model may be used, in turn, to improve processing of new uncalibrated data, e.g., by reporting the likely accuracy of the data or conditionally processing the uncalibrated data based on the likelihood of being accurate.

As shown in step 1102, the method 1100 may include obtaining calibrated physiological data from a first type of physiological monitors assumed to be accurate. For example, this may include obtaining calibrated heart rate data from a number of subjects using one or more chest strap type sensors, which provide a generally accepted measure of heart rate that is assumed, e.g., for medical purposes, to accurately reflect the heart rate of a subject over time. The number of subjects may usefully include a relatively large number of subjects, with data acquired over a relatively wide range of different activity types and activity intensities. In this manner, a useful training set can be obtained for use with machine learning algorithms to derive, e.g., a quality estimator engine.

As shown in step 1104, the method may include obtaining uncalibrated physiological data from a second type of physiological monitors of unknown accuracy. For example, this may include obtaining uncalibrated heart rate data from the number of subjects discussed above concurrently with the calibrated heart rate data using one or more physiological monitors of a wrist-worn photoplethysmography type. While wrist-worn devices are one common form of wearable physiological monitoring device, this may also or instead include wearable devices for any other limb, extremity, or part of the body. For example, this may include a wearable device strapped to a bicep, a thigh, an ankle, or the like. Useful heart rate data has also been acquired, e.g., from the ear or other locations, and any corresponding, suitably adapted wearable monitor may be used as a source of uncalibrated physiological data as contemplated herein.

As shown in step 1106, the method 1100 may include obtaining feature data. For example, this may include at least one signal used to estimate a heart rate with the uncalibrated heart rate data, such as time domain or frequency domain data for the physiological signal of interest, descriptive statistics for such signals, signals from a motion sensor, or any other signal or combination of signals from the sensors for a wearable device or the like. In one aspect, obtaining feature data may more specifically include obtaining feature data from one or more sensors of one or more physiological monitors of the wrist-worn photoplethysmography type described above, which may be acquired concurrently with the calibrated heart rate data and the uncalibrated heart rate data. The feature data may also or instead include at least one value derived from a signal from one of the physiological monitors of the wrist-worn photoplethysmography type, or a signal derived from a motion sensor of one of the physiological monitors of the wrist-worn photoplethysmography type. More generally, the feature data may include any data characterizing a timewise data acquisition context for the uncalibrated physiological data such as any of the data described above.

As shown in step 1108, the method 1100 may include associating a quality metric with the uncalibrated physiological data (e.g., the uncalibrated heart rate data). In general, this may be any quality metric indicative of the accuracy of the uncalibrated physiological data. For example, the quality metric may indicate whether uncalibrated heart rate data is within a predetermined threshold (e.g., a number of beats per minute) of the calibrated heart rate data, or within some other predetermined threshold of some other physiological measurement value. The quality metric may be associated in a timewise manner suitable for processing as contemplated herein. For example, this may include comparing calibrated data to uncalibrated data over a window, for an instantaneous measurement, for an average over some time period, or some combination of these.

As shown in step 1110, the method 1100 may include creating a quality estimator engine to evaluate a likelihood of the uncalibrated heart rate data being accurate based on the feature data. This may include creating a model using any of the techniques described herein. For example, creating the quality estimator engine may include training a machine learning decision tree or random forest to estimate the quality metric for a set of feature data. More generally, creating the model may include training a quality estimator engine to determine a quality of the uncalibrated physiological data (e.g., a likelihood of accuracy) based on the feature data and a difference between the uncalibrated physiological data and the calibrated physiological data. In this context, the quality metric may initially be assigned to the training set as a binary value. For example, the quality metric may be a one when the uncalibrated heart rate data is within the predetermined threshold of the uncalibrated heart rate data, and a zero when the uncalibrated heart rate data is not within the predetermined threshold of the uncalibrated heart rate data. Based on this training data, other feature sets within the feature space may be evaluated using the quality estimator engine to estimate the likelihood of also being accurate.

Creating the model may also or instead include customizing the model to a particular user. For example, the method 1100 may include characterizing a particular user of the physiological monitor based on, e.g., fitness, average level of activity, demographics (age, height, weight, gender, etc.), and so forth. The method 1100 may then include identifying a subset of the number of subjects that provided the training data that are most similar to the user. This subset of subjects may then be used to associate a quality metric for the uncalibrated heart rate data with the feature data for the subset, e.g., by training a machine learning model based specifically on the subset of subjects that are similar to the target user. In this manner, the model can be customized or optimized to a particular user so that the likelihood of being accurate is more closely fitted to the activity level and object characteristics of the current user.

Once trained or otherwise configured or created, the quality estimator engine 1112 may be stored in a memory for subsequent use. This may include storing the model on a server or remote resource for use in cloud-based calculations, or storage on a wearable device for use in real time, local data acquisition calculations.

As shown in step 1114, the method 1100 may include receiving data from a wearable device. This new data, including data from a different user or a different physiological monitor, referred to herein as "second uncalibrated heart rate data" for the heart rate monitor described above, may be evaluated for accuracy using the quality estimator engine described above. In general, the wearable device may be a device of the same type as the source(s) of uncalibrated physiological data used for the training sets discussed above. For example, this may be a wrist-worn heart rate monitor using photoplethysmography or the like to obtain heart rate data for a user over time. The data may include uncalibrated data, e.g., the physiological signal(s) of interest, and feature data indicative of the data acquisition context. As noted above, the feature data may include or be based on the physiological signal(s), or may be obtained from other sensors on the wearable device. It will be understood that, while the quality estimator engine usefully generalizes the data quality evaluation model for general use, the data received in step 1114 may also or instead include new data from one of the users or devices from the training set.

As shown in step 1116, the method 1100 may include determining data quality for the second uncalibrated data, such as a probability that the second uncalibrated data is accurate. For example, this may include calculating a probability that the physiological data is accurate for a window of measurements by applying the quality estimator engine to a distribution of values for the physiological data and corresponding values for the feature data. In one embodiment, this may include determining a probability that the second uncalibrated heart rate data described above is accurate for a window of measurements by calculating a conditional probability that the second uncalibrated heart rate data is accurate based on the corresponding second feature data over a distribution of values for the calibrated heart rate data within the window of measurements based on the quality estimator engine. In general, while the likelihood of accuracy may usefully be calculated over a distribution of measurements (and corresponding feature data measurements) for the window, instantaneous measurements may also or instead be evaluated with the quality estimator engine and used for subsequent processing.

As shown in step 1118, the method 1100 may include associating the probability, e.g., the likelihood of being accurate within a predetermined threshold, with the window as a measure of quality for the newly acquired uncalibrated heart rate data within the window.

As shown in step 1120, the method 1100 may include providing feedback to a user based on the measure of quality for the uncalibrated data. For example, this may include providing feedback to a user concerning an adjustment to the wearable device or other physiological monitor such as a change in position or a change in tension for a band that is used to secure the physiological monitor to the user's body.

As shown in step 1122, the method 1100 may include other quality-based processing. For example, the method 1100 may include conditionally processing the physiological data based on the measure of quality. For example, if a calculation requires a threshold of accuracy, only windows of data with at least the corresponding threshold of accuracy will be used for the corresponding calculation. In another aspect, where data quality is sufficiently degraded, processing may cease, or a user may be notified of the poor data quality. In another aspect, metrics such as recovery and strain described above may be weighted according to data quality. For example, weights may be assigned to each physiological measurement according to the absolute value of the data quality (e.g., likelihood of being accurate), based on a trend in data quality, or some combination of these. Similarly, some data may be excluded if the data quality falls below a predetermined threshold, or if the data quality for a particular segment is substantially below timewise adjacent segments of calculated or estimated physiological data.

As a significant advantage, quality-based processing as described herein permits the explicit selection of more accurate physiological data when calculating derivative metrics for strain, sleep, recovery and so forth. This creates a corresponding increase in signal-to-noise ratio for quantitative calculations by enabling targeted removal or exclusion of data points or timewise data segments that are likely to be inaccurate. The resulting improvements in the quantitative and qualitative user feedback about physical states can enable improved athletic conditioning and performance when compared to users who are obtaining data from similar wearable devices without corresponding countermeasures for data that is likely to be inaccurate. These techniques may also or instead be used, e.g., to facilitate user selection of thresholds for data accuracy when calculating derivative metrics, when displaying physiological data, when providing qualitative feedback, and so forth. For example, computer-generated feedback may be modified to qualify narrative results, e.g., by saying "you accumulated a sleep deficit of thirty minutes this week, however, your sleep data for the past two days is highly inaccurate and may result in incorrect assessments of actual rest."

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A computer program product comprising computer executable code embodied in a non-transitory computer readable medium that, when executing on one or more computing devices, performs the steps of:

receiving optical data and motion data from a photoplethysmography monitor worn substantially continuously by a user;

processing the optical data to obtain heart rate data for the user;

analyzing a sleep performance over a historical time window based on the heart rate data and the motion data and calculating a baseline sleep need for the user based on the sleep performance over the historical time window;

calculating a first sleep debt metric based on an objective measure of strain experienced by the user during an interval preceding a most recent sleep cycle;

calculating a second sleep debt metric as an accumulation of prior sleep debt relative to the baseline sleep need over one or more preceding sleep cycles; and calculating a sleep need for the user based on the first sleep debt metric, the second sleep debt metric, and a pattern-determined sleep need, wherein the pattern-determined sleep need includes at least one of a biologically-determined sleep need, a habitual sleep need, and an actual sleep pattern for the user over time.

2. The computer program product of claim 1, wherein the second sleep debt metric is calculated based on at least a sleep duration.

3. The computer program product of claim 1, wherein the second sleep debt metric is calculated based on at least a sleep onset latency.

4. The computer program product of claim 1, wherein the second sleep debt metric is calculated based on at least a number of waking intervals over the most recent sleep cycle.

5. The computer program product of claim 1, wherein calculating the sleep need for the user includes calculating the sleep need with a remote server coupled in a communicating relationship with the photoplethysmography monitor.

6. The computer program product of claim 5, further comprising transmitting the sleep need to a computing device associated with the user for display to the user.

7. A method for determining a sleep need, the method comprising:

receiving physiological data from a wearable device worn substantially continuously by a user, the physiological data including at least heart rate data;

analyzing a sleep performance over a historical time window based on the physiological data and calculating a baseline sleep need for the user based on the sleep performance over the historical time window;

calculating a first sleep debt metric based on an objective measure of strain experienced by the user during an interval preceding a most recent sleep cycle;

calculating a second sleep debt metric as an accumulation of prior sleep debt relative to the baseline sleep need over one or more preceding sleep cycles; and calculating the sleep need for the user based on the first sleep debt metric, the second sleep debt metric, and a pattern-determined sleep need.

8. The method of claim 7, wherein the physiological data includes motion data detected with one or more motion sensors in the wearable device.

9. The method of claim 8, wherein the one or more motion sensors include at least one or more gyroscopes or one or more accelerometers.

10. The method of claim 7, wherein the physiological data includes optical data from one or more optical sensors of the wearable device, the method further comprising processing the optical data to obtain the heart rate data.

11. The method of claim 10, wherein the heart rate data includes one or more of a representative resting heart rate for the user and a representative heart rate variability for the user, wherein the optical data is used to obtain the heart rate data.

12. The method of claim 7, wherein the pattern-determined sleep need includes a biologically-determined sleep need.

13. The method of claim 7, wherein the pattern-determined sleep need includes a habitual sleep need.

14. The method of claim 7, wherein the pattern-determined sleep need includes an actual sleep pattern for the user over time.

15. The method of claim 7, wherein the second sleep debt metric is calculated based on a time spent in one or more stages of sleep over the most recent sleep cycle.

16. The method of claim 7, wherein the second sleep debt metric is calculated based on at least one of a sleep duration and a sleep onset latency.

17. The method of claim 7, wherein the physiological data used to calculate the baseline sleep need is taken from a plurality of days from the historical time window where activity by the user did not exceed a predetermined strain level.

18. A system, comprising:

a wearable physiological monitoring device; and a processor and a memory storing computer executable code that, when executed by the processor, performs the steps of:

receiving physiological data from a wearable device worn substantially continuously by a user, the physiological data including at least heart rate data, analyzing a sleep performance over a historical time window based on the physiological data and calculating a baseline sleep need for the user based on the sleep performance over the historical time window, calculating a first sleep debt metric based on an objective measure of strain experienced by the user during an interval preceding a most recent sleep cycle, calculating a second sleep debt metric as an accumulation of prior sleep debt relative to the baseline sleep need over one or more preceding sleep cycles, and calculating a sleep need for the user based on the first sleep debt metric, the second sleep debt metric, and a pattern-determined sleep need.

19. The system of claim 18, wherein the processor executes on a server coupled in a communicating relationship with the wearable physiological monitoring device.

20. The system of claim 18, wherein the objective measure of the strain is scaled to minutes representing an additional duration of the sleep need for the user resulting from the strain experienced by the user and wherein the objective measure of the strain is scaled from 0 to 21, and wherein the first sleep debt metric, $f(i)$, is calculated using a formula of:

$$f(i) = \frac{1.7}{1 + e^{\frac{17-i}{3.5}}}$$

wherein i is the objective measure of the strain.

* * * * *